US012806027B2

(12) United States Patent
Yadav et al.

(10) Patent No.: US 12,806,027 B2
(45) **Date of Patent: *Nov. 24, 2026**

(54) ROBOTIC SHOULDER FRACTURE MANAGEMENT

(71) Applicant: Howmedica Osteonics Corp., Mahwah, NJ (US)

(72) Inventors: Rajan Yadav, New Delhi (IN); Koustubh Rao, Davie, FL (US); Andrew J. Nelson, New City, NY (US); David Viscardi, Glen Rock, NJ (US); Jetinder Singh, Gurgaon (IN)

(73) Assignee: HOWMEDICA OSTEONICS CORP., Mahwah, NJ (US)

(*) Notice: Subject to any disclaimer, the term of this patent is extended or adjusted under 35 U.S.C. 154(b) by 421 days.

This patent is subject to a terminal disclaimer.

(21) Appl. No.: 18/630,454

(22) Filed: Apr. 9, 2024

(65) Prior Publication Data

US 2024/0341966 A1 Oct. 17, 2024

Related U.S. Application Data

(63) Continuation of application No. 18/070,558, filed on Nov. 29, 2022, now Pat. No. 11,980,549, which is a (Continued)

(51) Int. Cl.
*A61B 17/72* (2006.01)
*A61B 34/00* (2016.01)
(Continued)

(52) U.S. Cl.
CPC ........ *A61F 2/4003* (2013.01); *A61F 2/30771* (2013.01); *A61F 2/30942* (2013.01); (Continued)

(58) Field of Classification Search
None
See application file for complete search history.

(56) References Cited

U.S. PATENT DOCUMENTS 7,785,328 B2 8/2010 Christie et al.
7,831,292 B2 * 11/2010 Quaid .................... A61B 34/37 345/157

(Continued)

FOREIGN PATENT DOCUMENTS

EP 1523964 A2 * 4/2005 ........... A61F 2/4657
EP 2258320 A2 12/2010

(Continued)

*Primary Examiner* — Ann Hu
(74) *Attorney, Agent, or Firm* — DUANE MORRIS LLP

(57) ABSTRACT

A method of repairing a fractured bone may include implanting a prosthetic stem into an intramedullary canal of the fractured bone. First and second bone segments of the fractured bone may be robotically machined to include first and second implant-facing surfaces that are substantially negatives of first and second surface portions of the first end of the prosthetic stem. The first and second tuberosities may be machined so that the first and second bone segments have first and second interlocking surfaces shaped to interlock with each other. During implantation, the first and second implant-facing surfaces are in contact with the first and second surface portions of the first end of the prosthetic stem, and the first interlocking surface interlocks with the second interlocking surface.

10 Claims, 16 Drawing Sheets

Related U.S. Application Data continuation of application No. 17/167,154, filed on Feb. 4, 2021, now Pat. No. 11,559,405.

(60) Provisional application No. 62/975,262, filed on Feb. 12, 2020.

(51) Int. Cl.
*A61B 34/30* (2016.01)
*A61B 90/00* (2016.01)
*A61F 2/30* (2006.01)
*A61F 2/40* (2006.01)
*A61F 2/46* (2006.01)

(52) U.S. Cl.
CPC ............ *A61F 2/4675* (2013.01); *A61B 17/72* (2013.01); *A61F 2002/4007* (2013.01); *A61F 2002/4632* (2013.01); *A61F 2310/00359* (2013.01)

(56) References Cited

U.S. PATENT DOCUMENTS 7,942,879 B2 5/2011 Christie et al.
8,167,882 B2 5/2012 Sackett et al.
8,403,934 B2 3/2013 Angibaud et al.
8,623,026 B2 1/2014 Wong et al.
8,753,346 B2 6/2014 Suarez et al.
8,828,003 B2 9/2014 Sackett et al.
8,968,409 B2 * 3/2015 Chavarria ............ A61F 2/4014 623/18.11
8,992,542 B2 3/2015 Hagag et al.
9,017,336 B2 4/2015 Park et al.
9,326,780 B2 5/2016 Wong et al.
9,597,157 B2 3/2017 Hagag et al.
9,603,711 B2 3/2017 Bojarski et al.
9,681,960 B2 * 6/2017 Olson .................... G01B 5/065
9,724,167 B2 8/2017 Ziaei et al.
9,770,306 B2 9/2017 Hagag et al.
9,808,318 B2 11/2017 Bonutti
9,861,446 B2 1/2018 Lang
9,980,780 B2 5/2018 Lang
10,052,166 B2 8/2018 Ziaei et al.
10,159,530 B2 12/2018 Lang
10,206,750 B2 2/2019 Hagag et al.
10,278,777 B1 5/2019 Lang
10,292,768 B2 5/2019 Lang
10,368,947 B2 8/2019 Lang
10,405,927 B1 9/2019 Lang
10,881,440 B2 * 1/2021 Bonutti ................. A61F 2/0805
11,129,645 B2 * 9/2021 Bonutti .............. A61B 17/0401
11,134,995 B2 * 10/2021 Bonutti .............. A61B 17/0401
11,266,503 B2 * 3/2022 Coulange ............ A61F 2/30942
11,559,405 B2 * 1/2023 Yadav ................... A61F 2/4003
11,980,549 B2 * 5/2024 Yadav .................... A61B 17/72
2005/0049710 A1 * 3/2005 O'Driscoll ............ A61F 2/3804 623/20.11
2005/0154331 A1 7/2005 Christie et al.
2005/0177241 A1 * 8/2005 Angibaud ............ A61F 2/4059 623/19.14
2007/0078516 A1 * 4/2007 Emami ................. A61F 2/4014 623/19.12
2007/0226986 A1 10/2007 Park et al.
2010/0082031 A1 4/2010 Sackett et al.
2010/0217400 A1 * 8/2010 Nortman ................ A61B 34/25 623/20.14
2010/0286696 A1 11/2010 Christie et al.
2011/0060341 A1 3/2011 Angibaud et al.
2011/0082462 A1 4/2011 Suarez et al.
2011/0082468 A1 4/2011 Hagag et al.
2011/0082587 A1 4/2011 Ziaei et al.
2011/0087332 A1 4/2011 Bojarski et al.
2012/0041446 A1 2/2012 Wong et al.
2012/0226281 A1 9/2012 Sackett et al.
2014/0114425 A1 * 4/2014 Ekelund ................ A61F 2/4059 623/19.14
2014/0163568 A1 6/2014 Wong et al.
2015/0100066 A1 * 4/2015 Kostrzewski ...... A61B 17/1615 606/130
2015/0164600 A1 6/2015 Hagag et al.
2015/0366594 A1 * 12/2015 Berghs ............... A61B 17/8061 606/281
2016/0242931 A1 8/2016 Wong et al.
2017/0189203 A1 7/2017 Hagag et al.
2017/0258526 A1 9/2017 Lang
2017/0333144 A1 11/2017 Ziaei et al.
2018/0014894 A1 1/2018 Hagag et al.
2018/0116728 A1 5/2018 Lang
2018/0125584 A1 5/2018 Lang
2018/0263704 A1 9/2018 Lang
2019/0110842 A1 4/2019 Lang
2019/0167356 A1 * 6/2019 Britton ................... A61B 34/35
2019/0175291 A1 6/2019 Hagag et al.
2019/0192226 A1 6/2019 Lang
2019/0240030 A1 * 8/2019 Coulange ............ A61F 2/30942
2019/0262078 A1 8/2019 Lang
2020/0121391 A1 * 4/2020 Forstein ................ A61F 2/4644
2020/0214747 A1 * 7/2020 Bonutti .............. A61B 17/0401
2020/0383793 A1 * 12/2020 Behzadi ............. A61B 17/7283

FOREIGN PATENT DOCUMENTS

EP 3228281 A1 * 10/2017 ........... A61F 2/4059
FR 2939639 A1 * 6/2010 ........... A61F 2/4014
FR 2965712 A1 * 4/2012 ........... A61F 2/4014
WO WO-2008116203 A2 * 9/2008 ......... A61B 17/7058
WO WO-2015131133 A1 * 9/2015 ............. G16H 20/40

* cited by examiner

ROBOTIC SHOULDER FRACTURE MANAGEMENT

CROSS-REFERENCE TO RELATED APPLICATIONS

This application is a continuation of U.S. patent application Ser. No. 18/070,558, filed Nov. 29, 2022, which is a continuation of U.S. patent application Ser. No. 17/167,154, filed on Feb. 4, 2021, which issued as U.S. Pat. No. 11,559,405 on Jan. 24, 2023, which claims the benefit of the filing date of U.S. Provisional Patent Application No. 62/975,262, filed Feb. 12, 2020.

BACKGROUND OF THE DISCLOSURE

Certain types of bone fractures and/or joint replacements may present particular difficulties. For example, a fracture of the proximal humerus and/or proximal femur may require the humeral or femoral head to be temporarily removed, an implant stem implanted into the shaft of the humerus or femur, and the humeral or femoral head replaced and fixed to the implant stem. If the fracture results in multiple tuberosities, they may need to be positioned correctly in relation to the implant stem and each other, and fixed together, for example via suturing. Similar procedures may need to be performed during shoulder or hip joint replacements, although in those procedures, the native humeral or femoral head (or a portion thereof) may need to be replaced with a corresponding prosthetic humeral or femoral head. However, current implant products and techniques rely heavily on individual subjective surgeon experience and may not optimize the placement of bone segments relative to one another and to the implant to which they will contact. Non-optimal positioning may lead to relative movement between the pieces of bone and/or the implant, which may slow healing and/or result in below optimal results for the patient.

BRIEF SUMMARY

A method of repairing a fractured humerus may include implanting a prosthetic humeral stem into a humeral canal of the fractured humerus, the humeral stem having a proximal end with a first surface portion and a second surface portion. A first tuberosity of the fractured humerus may be robotically machined to include a first implant-facing surface that is substantially a negative of the first surface portion of the proximal end of the prosthetic humeral stem. A second tuberosity of the fractured humerus may be robotically machined to include a second implant-facing surface that is substantially a negative of the second surface portion of the proximal end of the prosthetic humeral stem. The first tuberosity and the second tuberosity may be machined so that the first tuberosity has a first interlocking surface and the second tuberosity has a second interlocking surface shaped to interlock with the first interlocking surface. The first tuberosity and the second tuberosity may be positioned with respect to the proximal end of the prosthetic humeral stem so that (i) the first implant-facing surface is in contact with the first surface portion of the proximal end of the prosthetic humeral stem, (ii) the second implant-facing surface is in contact with the second surface portion of the proximal end of the prosthetic humeral stem, and (iii) the first interlocking surface interlocks with the second interlocking surface.

The first tuberosity may be held within a fixture while the first tuberosity is robotically machined to include the first implant-facing surface and the first interlocking surface. At least one tracking device may be coupled to the fixture while the first tuberosity is held within the fixture. A position of the first tuberosity may be registered while it is held within the fixture and prior to robotically machining the first tuberosity. The first interlocking surface may include a protrusion, and the second interlocking surface may include a recess to receive the protrusion. The first interlocking surface may interlock with the second interlocking surface, the first and second interlocking surfaces may restrict the first tuberosity from moving in medial and lateral directions relative to the second tuberosity. The first interlocking surface may interlock with the second interlocking surface, the first and second interlocking surfaces may restrict the first tuberosity from moving in an axial direction relative to the second tuberosity, the axial direction being substantially parallel to a longitudinal axis of the implanted humeral stem.

The first tuberosity may be robotically machined to have a first suture hole, and the second tuberosity may be robotically machined to have a second suture hole. At least one suture may be passed through the first suture hole, through the second suture hole, and through an implant suture hole positioned within the proximal end of the prosthetic humeral stem. After the at least one suture is passed through the first suture hole, through the second suture hole, and through the implant suture hole, the at least one suture may be manipulated to draw the first tuberosity and the second tuberosity into contact with the proximal end of the prosthetic humeral stem. Passing the at least one suture through the first suture hole, through the second suture hole, and through the implant suture hole may be performed by an end effector coupled to a robotic device. The first suture hole and the second suture hole may each be configured to have a position corresponding to a position of the implant suture hole while the prosthetic humeral stem is implanted into the humeral canal and while the first tuberosity and the second tuberosity are both in contact with the proximal end of the prosthetic humeral stem. A proximal end surface of the fractured humerus may be robotically machined to have a first mating feature, and the first tuberosity of the fractured humerus may be robotically machined to include a second mating feature on a distal portion of the first tuberosity, the first mating feature adapted to interlock with the second mating feature.

An adhesive may be applied to the first interlocking surface and to the second interlocking surface. The adhesive may be bone cement. The first interlocking surface and the second interlocking may each include peaks and troughs. The first interlocking surface may have a press-fit relationship with the second interlocking surface when the first interlocking surface engages the second interlocking surface.

DETAILED DESCRIPTION

In describing preferred embodiments of the disclosure, reference will be made to the directional nomenclature used in describing the human body. It is noted that this nomenclature is used only for convenience and that it is not intended to be limiting with respect to the scope of the invention. When referring to specific directions in relation to a device, the device is understood to be described only with respect to its orientation and position during an exemplary application to the human body. As used herein when referring to bones or other parts of the body, the term "proximal" means closer to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body. Further, although the devices and methods described herein are generally described in relation to human shoulder repair or replacement, it should be understood that the devices and methods are not intended to be so limited and could be used with other joints, such as other ball and socket joints, including the hip, for example.

Figure 1:
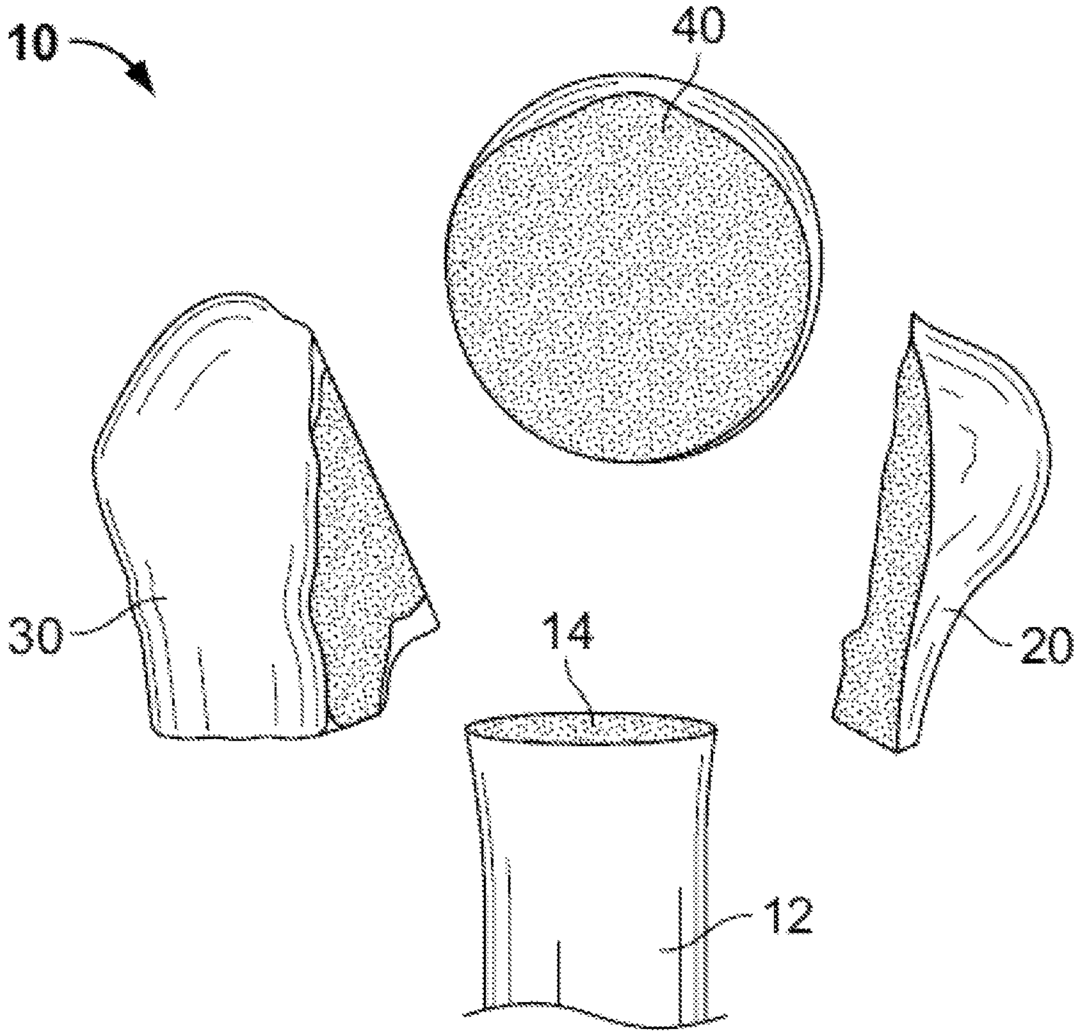
FIG. 1 is a schematic view of an exemplary proximal humerus broken into a plurality of bone fragments.

Generally, the replacement of a humeral head with a prosthetic implant during shoulder arthroplasty involves gaining access to the shoulder joint through a retracted incision and removing the damaged humeral head. An exemplary damaged proximal humerus 10 is illustrated in FIG. 1. Although such breaks giving rise to a plurality of bone fragments may occur in any number of ways, this particular humerus 10 is broken such that a first segment 20, a second segment 30, and a third segment 40 including a substantial portion of the humeral head are each detached from the proximal end 12 of the humerus. These bone segments may also be referred to as tuberosities. After removal of the humeral head 40, the proximal end of the humeral medullary canal may be shaped in order to accept an implant according to known methods. In one exemplary method, a hand reamer, for example, may be used at a proximal humeral bearing surface 14 to remove bone material until an appropriately-shaped opening is formed in the proximal end 12 of humerus 10 for receiving an implant. Typically, successive reamers of increasing size are used in order to form an opening of the desired size. In many cases, bearing surface 14 may not be as flat as shown. Most surfaces at a fracture site are irregularly shaped unless there is a clean break between adjacent fragments. Such a surface may be resected into a generally flat shape to receive a corresponding bearing surface of a trial and/or implant stem as shown in FIG. 1. Once an appropriate bearing surface 14 and opening is formed for receiving an implant, a stem of a prosthesis may be inserted into the shaft of the humerus 10.

Figure 2A:
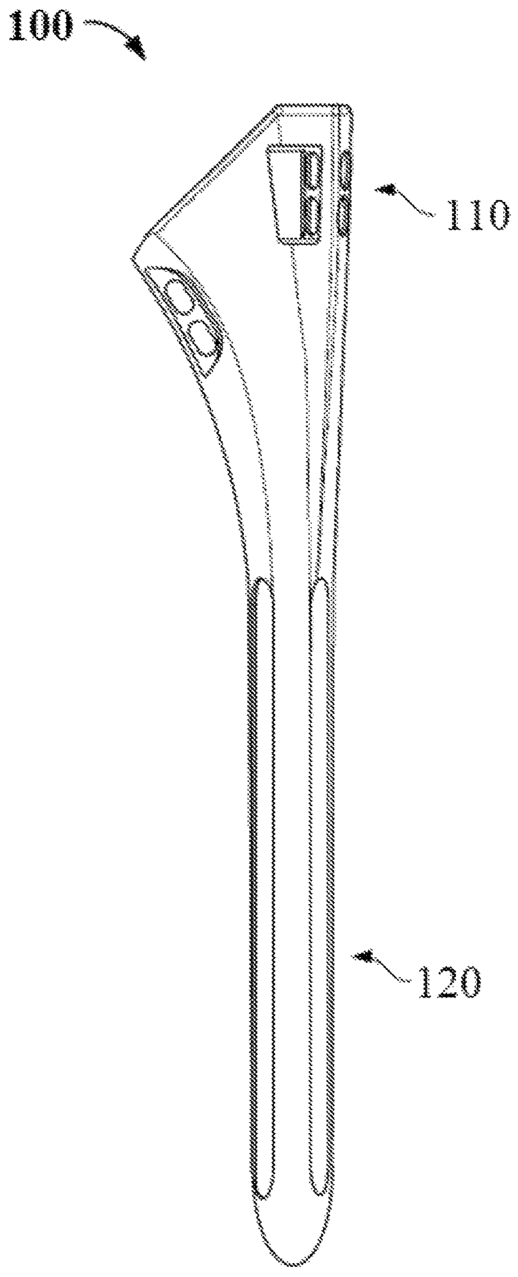
FIG. 2A is a perspective view of one embodiment of a stem implant according to aspects of the disclosure.
Figure 2B:
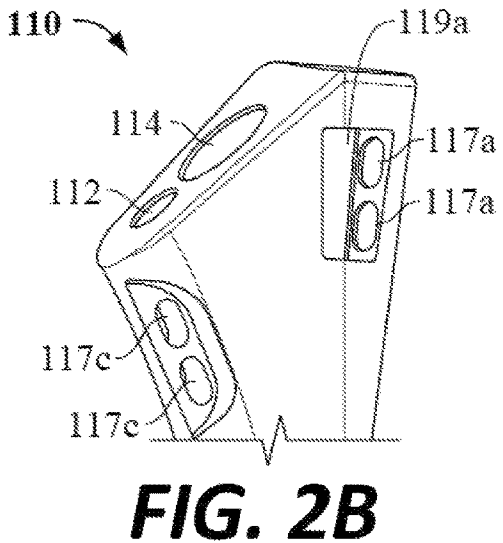
FIG. 2B is a perspective view of a proximal portion of the stem implant of FIG. 2A.
Figure 2C:
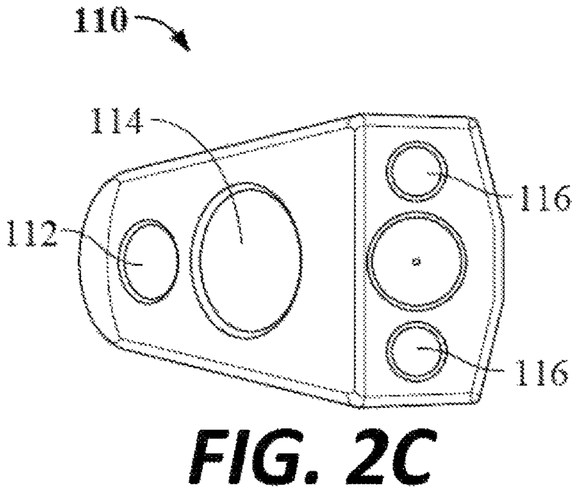
FIG. 2C is a top view of the stem implant of FIG. 2A.
Figure 2D:
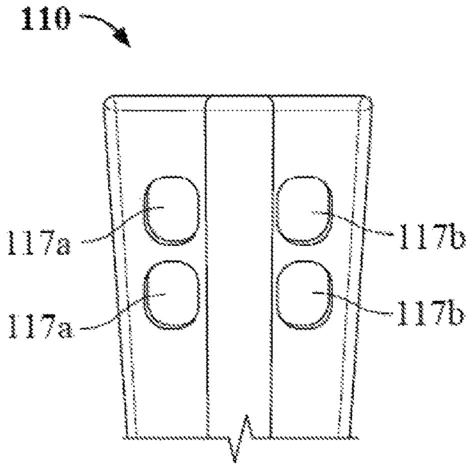
FIG. 2D is a side view of a proximal portion of the stem implant of FIG. 2A.

An exemplary embodiment of stem implant 100 is illustrated in FIG. 2A. Stem implant 100 may be monolithic with a proximal portion 110 and a distal portion 120. Proximal portion 110 of stem implant 100, shown in greater detail in FIGS. 2B-D, may include a catch aperture 112, an implant recess 114, and two locking pin apertures 116. The apertures 112, 116 may facilitate the connection between a handle or insertion system, such as that described in greater detail in U.S. Pat. No. 9,681,960, the disclosure of which is hereby incorporated by reference herein. Implant recess 114 may be configured to accept a humeral head implant, reverse cup humeral implant, or other compatible implant. Proximal portion 110 may also include a number of features to facilitate securing portions of humerus 10, such as first segment 20 and second segment 30, to stem implant 100. For example, a first pair of suture holes 117*a* may be formed on a lateral-anterior side of proximal portion 110 and a second pair of suture holes 117*b* may be formed on a lateral-posterior side of the proximal portion. A third pair of suture holes 117*c* may be formed on a medial side of proximal portion 110. The suture holes 117*a-c* may facilitate securing one or more bone fragments to stem implant 100 via suture wires (not illustrated). One suture pocket 119*a* may be formed on the lateral-anterior side of proximal portion 110, and may be connected to suture holes 117*a*. Another suture pocket (not visible in FIGS. 2A-D) may be formed on the lateral-posterior side of proximal portion 110, and may be connected to suture holes 117*b*. The suture pockets may, for example, facilitate the insertion of a suture needle. Typically the one or more sutures used to secure the one or more bone segments 20, 30, 40 to the proximal portion 110 of stem 100 are passed through apertures created in the bone segments. The one or more sutures may thus help secure the one or more bone segments 20, 30, 40 into close contact with each other and/or the proximal portion 110 of stem 100. However, as noted above, the outcome of such a procedure may rely significantly on the experience of the surgeon, and in all cases, the fragments 20, 30, 40 may tend to move relative to one another and/or the proximal portion 110 of stem 100, which may reduce the success of the procedure and the healing time for the patient.

In one embodiment, one or more broken fragments of a bone may be machined with the assistance of a robotic surgical tool, and the bone to which the broken fragment is to be re-attached is machined in a manner complementary to the fragment to create a complementary contact surfaces, for example a self-locking fit. In this example, a prosthetic implant is not needed and is thus not shown or described. However, as will become clear in other embodiments described below, similar concepts may be used in a procedure in which bone fragments are to be coupled to a prosthesis.

Figure 3:
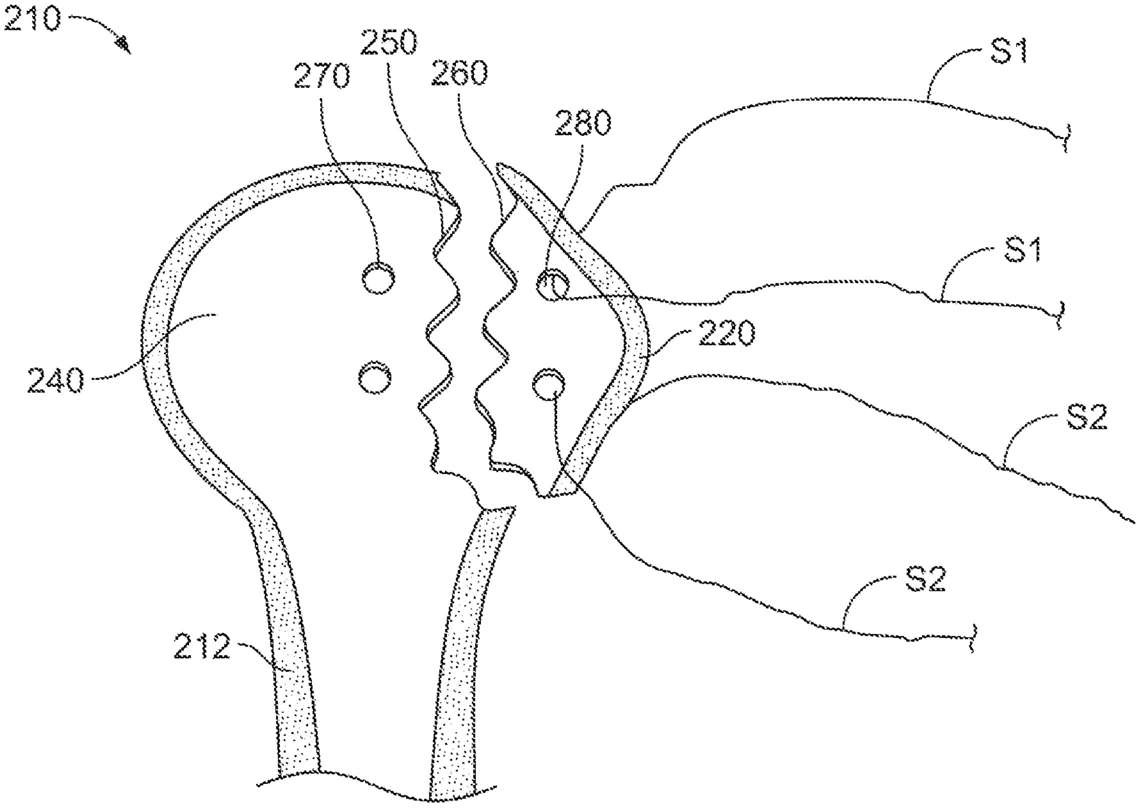
FIG. 3 is a schematic view of a broken proximal humerus with segments having self-locking features.

FIG. 3 is a highly schematic view of a portion of a damaged humerus 210, similar to humerus 10. For example, the proximal humerus 212 has the humeral head 240 mostly intact, with a single broken fragment (or tuberosity) 220 that forms a portion of the humeral head 240. In this exemplary fracture repair, an implant stem similar to that shown and described in connection with FIGS. 2A-D is not used. Rather, one or more first mating features 250 are formed in an exposed surface of the humeral head 240, and one or more complementary second mating features 260 are formed in fragment 220. In the illustrated embodiment, first mating features 250 include a plurality of peaks and troughs, and second mating features 260 include a corresponding plurality of peaks and troughs, with the peaks of first mating features 250 shaped and positioned to fit within the troughs of second mating features 260, and vice versa. With this configuration, the fragment 220 may contact the proximal humerus 212 so that the fragment 220 effectively fits with the remaining portion of the proximal humerus 212 like a puzzle piece, where the fragment 220 fits in substantially only one position and orientation relative to the proximal humerus 212. Further, when the fragment 220 is in the desired contact position and orientation with the proximal humerus 212, the first mating features 250 and second mating features 260 engage one another in a self-locking fashion, so that the fragment 220 will not move significantly relative to the proximal humerus 212 unless an intentional force is applied to reposition or remove the fragment 220. Although the first mating features 250 and second mating features 260 are illustrated as alternating peaks and troughs, various other interlocking shapes may be suitable, such as dovetail configurations, projections (or ribs) and corresponding recesses, etc. Similarly, the first mating features 250 and second mating features 260 may be machined to have a press- or interference-fit relationship to better secure the fragment 220 to the proximal humerus 212.

In the embodiment illustrated in FIG. 3, one or more suture apertures 270 are formed in the humeral head 240, and one or more corresponding suture apertures 280 are formed in fragment 220. The suture apertures 270, 280 may be formed manually, via a drill or similar tool, or formed with a robotic assistance, which may be the same or a similar device used to form first features 250 and second features 260. The suture apertures 270, 280 are preferably formed with robotic assistance to ensure that the suture apertures 270, 280 are positioned in the desired positions relative to each other. In the illustrated embodiment, proximal humerus 212 includes a proximal suture aperture 270 and fragment 220 includes a corresponding proximal suture aperture 280. A first suture S1 may be passed through the proximal suture aperture 280 in the fragment 220 and also through the proximal suture aperture 270 in the proximal humerus 212. Similarly, a second suture S2 may be passed through a distal suture aperture 280 in the fragment 220 and also through a distal suture aperture 270 in the proximal humerus 212. When the fragment 220 is coupled to the proximal humerus 212 so that first mating features 250 engage second mating features 260, the sutures S1 and S2 may be pulled taut and tied to maintain the fragment 220 in the desired engagement position and orientation with the proximal humerus 212. The sutures S1 and S2 help maintain the fragment 220 in close contact with the proximal humerus 212, and the first mating features 250 and second mating features 260 help ensure that there is no or minimal movement between the fragment 220 and the proximal humerus 212. Although the humerus 210 in FIG. 3 is illustrated with two suture apertures 270 in the proximal humerus 212, two suture apertures 280 in the fragment 220, and two sutures S1, S2, it should be understood that a one-to-one correspondence between suture holes 270 and suture holes 280 is not necessary, nor is a one-to-one correspondence between the suture holes 270, 280 and the number of sutures S1, S2.

Although first mating features 250 and second mating features 260 may be formed manually, it is preferable that they are formed with robotic assistance to help ensure that the fragment 220 has an optimal fit with proximal humerus 212. Prior to describing the creation of first mating features 250 and second mating features 260, an exemplary computer-assisted surgery system is described.

Figure 4:
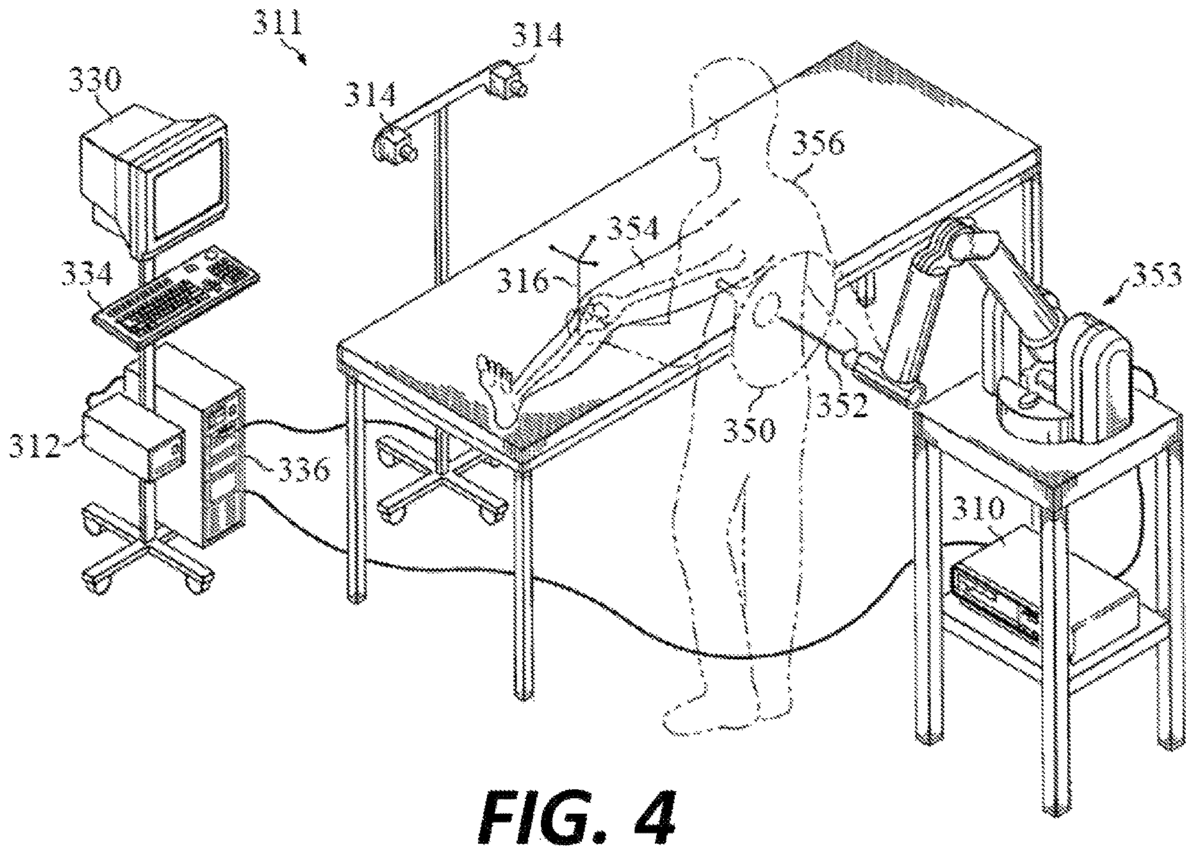
FIG. 4 is a diagrammatic illustration of an exemplary operating room in which a haptic device is used with a computer-assisted surgery system.

FIG. 4 is a diagrammatic illustration of an exemplary operating room in which a haptic device 353 is used with a computer-assisted surgery system 311. Computer-assisted surgery system 311 may include a display device 330, an input device 334, and a processor based system 336, for example a computer. Input device 334 may be any suitable input device including, for example, a keyboard, a mouse, or a touch screen. Display device 330 may be any suitable device for displaying two-dimensional and/or three-dimensional images, for example a monitor or a projector. If desired, display device 330 may be a touch screen and be used as an input device. One example of a system incorporating a haptic device 353 is described in greater detail in U.S. Pat. No. 7,831,292, the disclosure of which is hereby incorporated by reference herein.

Haptic device 353 is, in the illustrated example, a robotic device. Haptic device 353 may be controlled by a processor based system, for example a computer 310. Computer 310 may also include power amplification and input/output hardware. Haptic device 353 may communicate with computer-assisted surgery system 311 by any suitable communication mechanism, whether wired or wireless.

Also shown in FIG. 4 is a storage medium 312 may be coupled to processor based system 336. Storage medium 312 may accept a digital medium which stores software and/or other data. A surgical tool or instrument 352 is shown coupled to haptic device 353. Surgical tool 352 is preferably mechanically coupled to haptic device 353, such as by attaching or fastening it. However, if desired, surgical tool 352 may be coupled, either directly or indirectly, to haptic device 353 by any other suitable method, for example magnetically. Surgical tool 352 may be haptically controlled by a surgeon remotely or haptically controlled by a surgeon 356 present in proximity to surgical tool 352, although autonomous control with surgeon oversight is possible as well. Surgical tool 352 may be, for example, a bur, saw, laser, waterjet, cautery tool, or other trackable tool capable of cutting or otherwise shaping or resecting patent tissue, including bone. Patient tissue and bone may be referred to interchangeably herein and may include cartilage, tendons, skin tissue, and/or bone whether it be cortical or cancellous bone.

Haptic object 350 is a virtual object used to guide and/or constrain the movement and operations of surgical tool 352 to a target area inside a patient's anatomy 354, for example the patient's leg. In this example, haptic object 350 is used to aid the surgeon 356 to target and approach the intended anatomical site of the patient. Haptic feedback forces may be used to slow and/or stop the surgical tool's movement if it is detected that a portion of surgical tool 352 will intrude or cross over pre-defined boundaries of the haptic object. Furthermore, haptic feedback forces can also be used to attract (or repulse) surgical tool 352 toward (or away from) haptic object 350 and to (or away from) the target. If desired, surgeon 356 may be presented with a representation of the anatomy being operated on and/or a virtual representation of surgical tool 352 and/or haptic object 350 on display 330.

The computer-assisted surgery ("CAS") system preferably includes a localization or tracking system that determines or tracks the position and/or orientation of various trackable objects, such as surgical instruments, tools, haptic devices, patients, donor tissue and/or the like. The tracking system may continuously determine, or track, the position of one or more trackable markers disposed on, incorporated into, or inherently a part of the trackable objects, with respect to a three-dimensional coordinate frame of reference. Markers can take several forms, including those that can be located using optical (or visual), magnetic or acoustical methods. Furthermore, at least in the case of optical or visual systems, location of an object's position may be based on intrinsic features, landmarks, shape, color, or other visual appearances, that, in effect, function as recognizable markers.

Any type of tracking system may be used, including optical, magnetic, and/or acoustic systems, which may or may not rely on markers. Many tracking systems are typically optical, functioning primarily in the infrared range. They may include a stationary stereo camera pair that is focused around the area of interest and sensitive to infrared radiation. Markers emit infrared radiation, either actively or passively. An example of an active marker is a light emitting diode ("LED"). An example of a passive marker is a reflective marker, such as ball-shaped marker with a surface that reflects incident infrared radiation. Passive systems may include an infrared radiation source to illuminate the area of focus. A magnetic system may have a stationary field generator that emits a magnetic field that is sensed by small coils integrated into the tracked tools.

With information from the tracking system on the location of the trackable markers, CAS system 311 may be programmed to be able to determine the three-dimensional coordinates of an end point or tip of a tool and, optionally, its primary axis using predefined or known (e.g. from calibration) geometrical relationships between trackable markers on the tool and the end point and/or axis of the tool. A patient, or portions of the patient's anatomy, can also be tracked by attachment of arrays of trackable markers. In the illustrated example, the localizer is an optical tracking system that comprises one or more cameras 314 that preferably track a probe 316. As shown in FIG. 4, cameras 314 may be coupled to processor based system 336. If desired, cameras 314 may be coupled to computer 310. Probe 316 may be a conventional probe. If desired, the probe may be rigidly attached to haptic device 353 or integrated into the design of haptic device 353.

In one implementation, processor based system 336 may include image guided surgery software to provide certain user functionality, e.g., retrieval of previously saved surgical information, preoperative surgical planning, determining the position of the tip and axis of instruments, registering a patient and preoperative and/or intraoperative diagnostic image datasets to the coordinate system of the tracking system, etc. Full user functionality may be enabled by providing the proper digital medium to storage medium 312 coupled to computer 336. The digital medium may include an application specific software module. The digital medium may also include descriptive information concerning the surgical tools and other accessories. The application specific software module may be used to assist a surgeon with planning and/or navigation during specific types of procedures. For example, the software module may display predefined pages or images corresponding to specific steps or stages of a surgical procedure. At a particular stage or part of a module, a surgeon may be automatically prompted to perform certain tasks or to define or enter specific data that will permit, for example, the module to determine and display appropriate placement and alignment of instrumentation or implants or provide feedback to the surgeon. Other pages may be set up to display diagnostic images for navigation and to provide certain data that is calculated by the system for feedback to the surgeon. Instead of or in addition to using visual means, the CAS system could also communicate information in other ways, including audibly (e.g. using voice synthesis) and tactilely, such as by using a haptic interface. For example, in addition to indicating visually a trajectory for a drill or saw on the screen, a CAS system may feed information back to a surgeon whether he is nearing some object or is on course with an audible sound. To further reduce the burden on the surgeon, the module may automatically detect the stage of the procedure by recognizing the instrument picked up by a surgeon and move immediately to the part of the program in which that tool is used.

The software which resides on computer 336, alone or in conjunction with the software on the digital medium, may process electronic medical diagnostic images, register the acquired images to the patient's anatomy, and/or register the acquired images to any other acquired imaging modalities, e.g., fluoroscopy to CT, MRI, etc. If desired, the image datasets may be time variant, i.e. image datasets taken at different times may be used. Media storing the software module can be sold bundled with disposable instruments specifically intended for the procedure. Thus, the software module need not be distributed with the CAS system. Furthermore, the software module can be designed to work with specific tools and implants and distributed with those tools and implants. Moreover, CAS system can be used in some procedures without the diagnostic image datasets, with only the patient being registered. Thus, the CAS system need not support the use of diagnostic images in some applications—i.e. an imageless application.

Haptic device 313, components thereof, or similar systems may be used to perform highly accurate bone resections, such as the creation of first mating features 250, second mating features 260, suture apertures 270, 280, or any other bone resections described herein.

In an exemplary procedure to repair the proximal humerus 212 shown in FIG. 3, the patient's proximal humerus 212 (including the fragment 220) may be imaged by any suitable modality, and models may be created with the assistance of CAS system 311. The desired shape and positions of the first mating features 250, second mating features 260, and/or suture apertures 270, 280 may be planned pre-operatively (or possibly intra-operatively) to provide the desired mating between the fragment 220 and the proximal humerus 212. Once the operative plan is established, the patient's proximal humerus 212 may be stabilized with respect to the operating table in any desired fashion to keep the proximal humerus 212 substantially immobile. One or more trackers may be coupled to the proximal humerus 212, and a probe or similar device may be used to map the model of the proximal humerus 212 to the position of the proximal humerus 212. This process may be referred to as registration, and may include matching landmarks on the bone to corresponding landmarks on the virtual model. With the proximal humerus 212 registered, the one or more trackers coupled to the proximal humerus 212 may assist the CAS system 311 in understanding the position and orientation of the proximal humerus 212 in the operating theater, even if some movement of the proximal humerus 212 occurs after the initial registration. Then, the surgeon may operate CAS system 311, including a cutting tool similar to surgical instrument 352, in order to form the first mating features 250 in the proximal humerus 212 with a high degree of precision in relation to the pre-operative plan. If desired, the CAS system 311 may be utilized to create the suture apertures 270 before or after creation of the first mating features 250.

Figure 5:
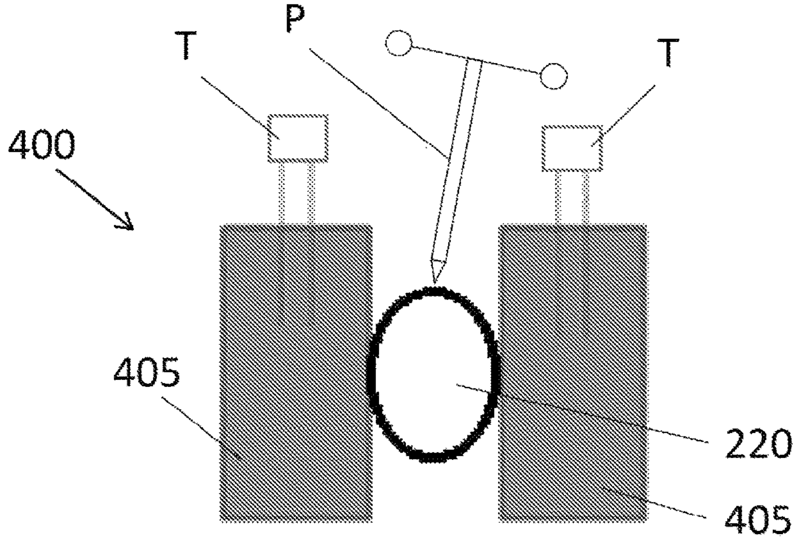
FIG. 5 is a highly schematic view of a fixture for holding bone for resection.

In order to create the second mating features 260 in the segment 220, the segment 220 may be removed from the patient and placed into a surgical fixture. For example, FIG. 5 illustrates a schematic diagram of a fixture 400 with fragment 220 positioned therein. Fixture 400 may take various appropriate forms, but generally may include at least two clamping members 405 that securely hold the fragment 220 therebetween, although other mechanisms may be suitable for holding fragment 220 in a substantially immobile position. One or more trackers may be positioned on the fixture 400, for example one tracker T on each clamp 405. Similar to the trackers described above, the trackers T may be tracked and/or "visualized" by the CAS system 311 in order to understand the exact positioning of the fixture 400 relative to the CAS system 311. After positioning the fragment 220 into the fixture 400, the fragment 220 may be registered to the CAS system 311. For example, a probe P may be used to determine the position and/or orientation of the fragment 220, which may be used to register the fragment 220 to the virtual model of the fragment. This may include using the probe P to touch off landmarks on the fragment 220 to match those landmarks to the corresponding landmarks in the virtual model of the fragment. In some embodiments, the fixture 400 may be physically or otherwise coupled to the CAS system 311 so that the position and/or orientation of the fixture 400 relative to the CAS system 311 is constant. In some embodiments, the fixture 400 may also be registered to the CAS system 311. In all embodiments, it is preferable that the fixture 400 hold the fragment 220 in a substantially fixed position and orientation that is understood and/or tracked by the CAS system 311 so that the CAS system 311, and particularly a tool thereof (such as surgical instrument 352) can precisely resect the fragment 220 (with or without assistance from the surgeon 356) so that the fragment 220 is machined to have the pre-operatively planned second mating features 260. The CAS system 311 may also create the one or more suture apertures 280 in the fragment 220, although in other embodiments the suture apertures 280 may be formed manually.

After the proximal humerus 212 is machined to have the first mating features 250, and the fragment 220 is machined to have the second mating features 260 (which may occur in any desired order), the fragment 220 may be placed in close proximity to the proximal humerus 212 so that the first mating features 250 and second mating features 260 begin to engage each other. Sutures S1 and S2 may be threaded through corresponding proximal and distal suture apertures 270, 280 in the proximal humerus 212 and the fragment 220. As the sutures are pulled, the fragment 220 will begin to pull toward the proximal humerus 212 with the first mating features 250 and second mating features 260 aligning and self-locking, reducing further motion of the fragment 220 relative to the proximal humerus 212. If desired, the first mating features 250 and/or second mating features 260 may be filled, sprayed, or otherwise provided with bone cement or other adhesive in order to strengthen the bond between the fragment 220 and the proximal humerus 212. The sutures S1 and S2 may be tied to complete the fixation of the fragment 220 to the proximal humerus 212. As should be understood from the above description, the interlocking features of the fragment 220 and the proximal humerus 212, as well as the position of the suture apertures 270, 280, may be pre-operatively designed to provide the optimal securement of the fragment 220 to the proximal humerus 212, and that pre-operative design may be precisely implemented with the use of CAS system 311. These features will provide for an objective best-fit between the fragment 220 and the proximal humerus 212, reducing or eliminating variation due to subjective choices of the surgeon.

Although the implementation of sutures S1 and S2 are described above as being performed manually, the CAS system 311 may instead be used to thread the sutures S1 and S2 through the suture apertures 270, 280. For example, if the CAS system 311 is used to create the suture apertures 270, 280, the CAS system 311 will have a complete understanding of the position and orientation of all suture apertures 270, 280 due to the data in the CAS system 311 and the tracking of the registered fragment 220 and proximal humerus 212. For example, a surgical tool 352 coupled to the CAS system 311 may include forceps, grips, or another manipulator which may hold sutures S1 and/or S2 and guide them through the suture apertures 270, 280.

Figure 6:
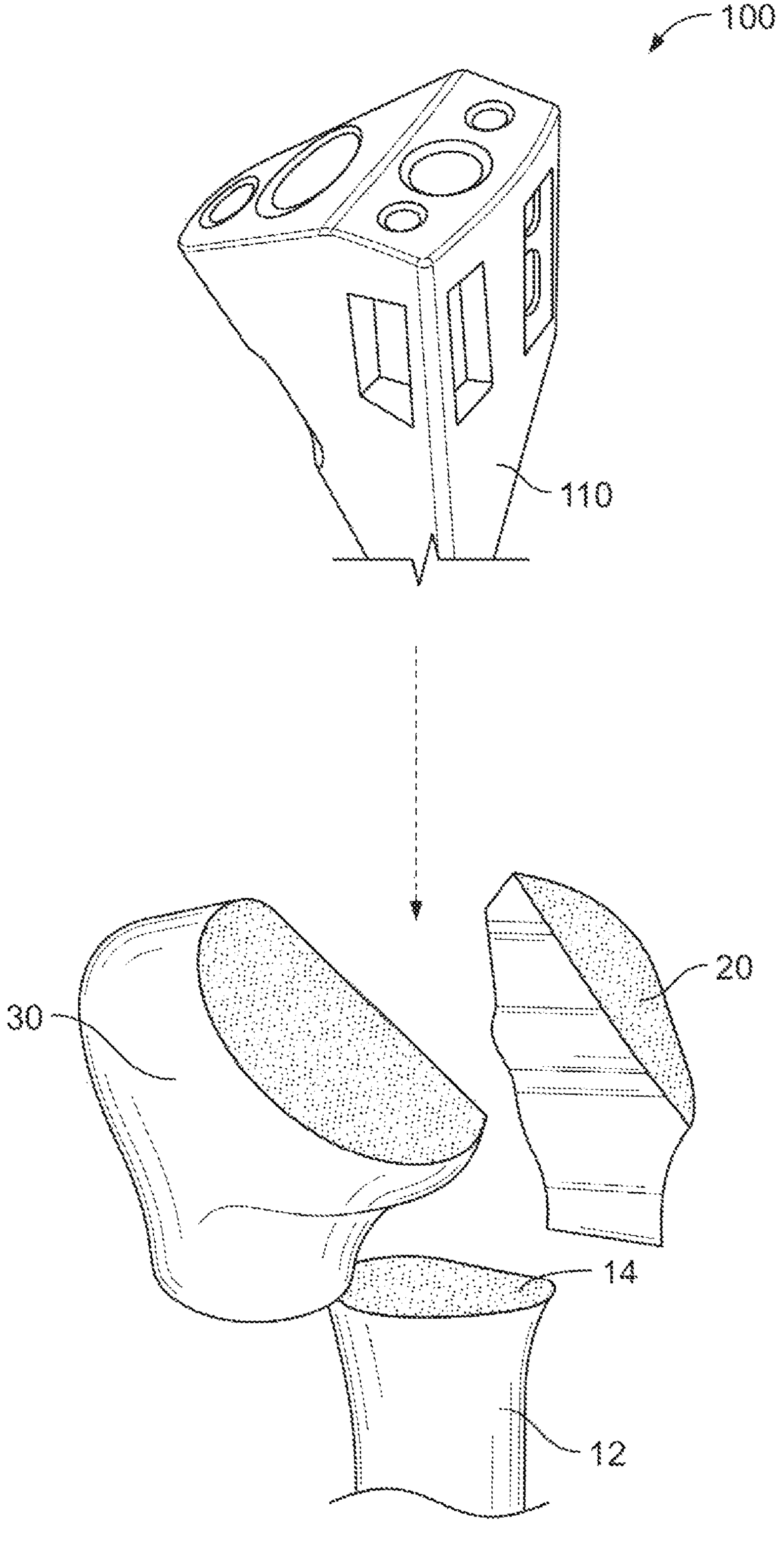
FIG. 6 is a highly schematic view of the stem implant of FIG. 2A relative to the proximal humerus of FIG. 1.

While one embodiment of the disclosure includes repair of a fracture without a prosthetic implant, the concepts described above can be applied for use during a joint replacement, which may include a fracture repair. For example, FIG. 6 illustrates a fractured humerus similar to that shown in FIG. 1 into which a prosthetic humeral stem 100 (only the proximal portion 110 of stem 100 illustrated in FIG. 6) will be inserted. In this exemplary procedure, after the prosthetic humeral stem 100 is inserted into the shaft of the proximal humerus 12, fragments 20, 30 will be reattached to the proximal portion 110 of the prosthetic humeral stem 100, and the humeral head fragment 40 (as illustrated in FIG. 1) will be replaced with a prosthetic humeral head (or a prosthetic humeral cup if the procedure calls for a reverse shoulder arthroplasty). Similar to the embodiment described above, the bone fragments 20, 30 preferably are robotically machined, for example using CAS system 311 (or a similar system) as described above, to have mating features that interlock with one another. The bone fragments 20, 30 may alternatively, or additionally, be machined to have surfaces that correspond to exterior surfaces of the proximal portion 110 of prosthetic humeral stem 100 to provide for enhanced coupling between the fragments 20, 30 and the proximal portion 110 of the humeral stem 100.

Figure 7:
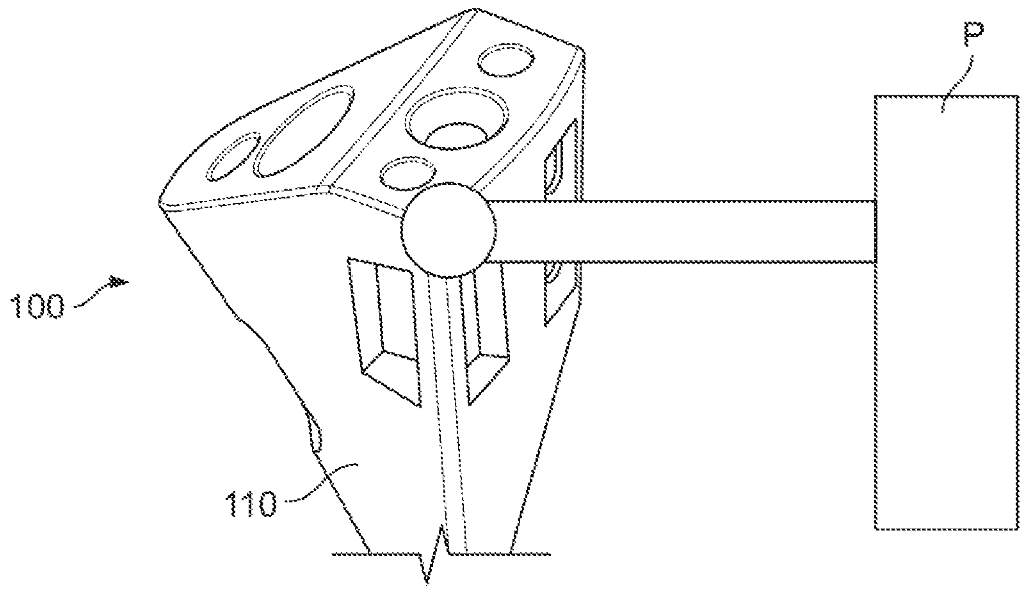
FIG. 7 is a highly schematic view of a probe in contact with the stem implant of FIG. 6.
Figure 8:
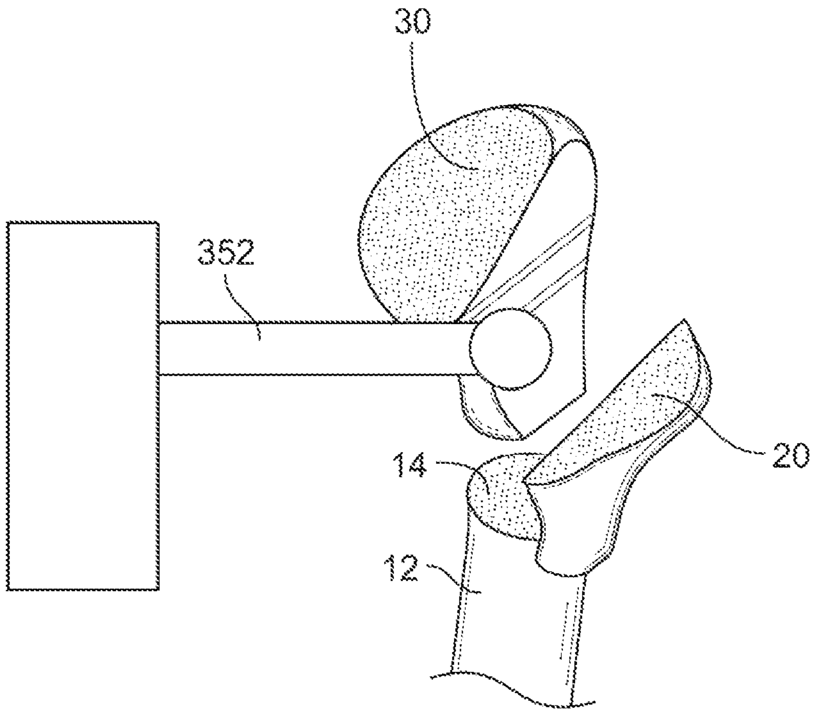
FIG. 8 is a highly schematic view of a surgical instrument machining the proximal humerus of FIG. 6.

Various methods may be suitable for machining fragments 20, 30 to have mating features that correspond to exterior surfaces of the proximal portion 110 of prosthetic humeral stem 100. In one example, the size, shape, dimensions, etc. of the entire prosthetic humeral stem 100 (or just the proximal portion 110 thereof) are known and/or stored on a system, such as storage medium 312. The known exterior surfaces may be used to machine the fragments 20, 30 to have corresponding surface geometries. For example, a negative of the proximal portion 110 of the prosthetic humeral stem 100 may be machined into the fragments 20, 30 so that little or no gap exists between the fragments 20, 30 and the prosthetic humeral stem 100 when the fragments 20, 30 are coupled to the prosthetic humeral stem 100. In other embodiments, as shown in FIG. 7, a probe P may be used to probe or scan the prosthetic humeral stem 100 in order to determine the relevant shapes, geometries, dimensions etc., which may then be used to machine corresponding shapes, geometries, and/or dimensions into the fragments 20, 30. As shown in FIG. 8, a surgical tool 352 of CAS system 311 may be used to machine the fragments 20, 30 in a similar fashion as described above or below to include mating features that mate with each other and/or to the proximal portion 110 of the humeral stem 100. Although not illustrated in FIG. 8, the fragments 20, 30 may be held in a fixture similar to that described in connection with FIG. 5 during the machining, and the machining may include creation of suture apertures (not illustrated) similar to the suture apertures described above.

Figure 9:
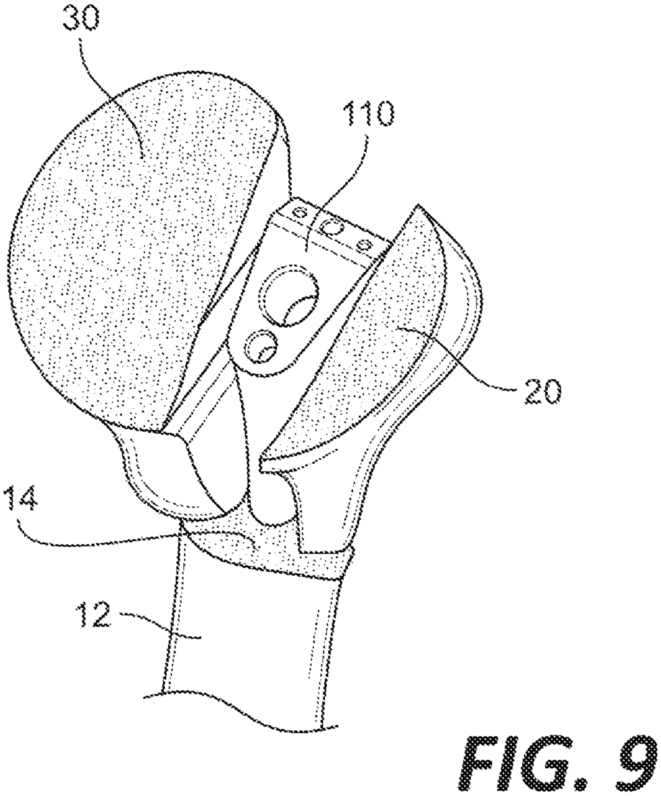
FIGS. 9-11 are perspective views of the stem implant of FIG. 6 in different stages of implantation into the proximal humerus of FIG. 6.
Figure 10:
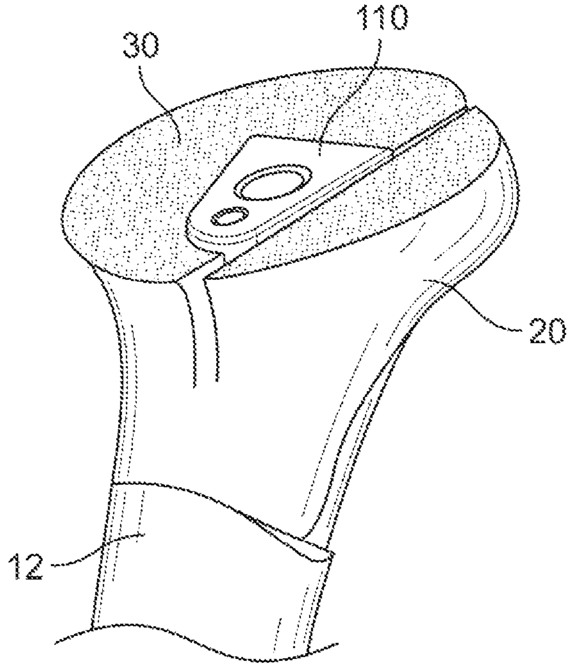

As shown in FIGS. 9-10, after the fragments 20, 30 have been machined, and the distal portion 120 of prosthetic humeral stem 100 has been implanted into the proximal humerus 12, the fragments 20, 30 may be brought into close contact with each other and with the proximal portion 110 of the prosthetic humeral stem 100. The mating features of fragment 20 may interlock with the mating features of fragment 30, and the mating features of fragments 20, 30 may also conform to the exterior surfaces of the proximal portion 110 of prosthetic humeral stem 100. This close engagement, as shown in FIG. 10, may allow for better bone ingrowth into the proximal portion 110 of the prosthetic humeral stem 100, reducing recovery time and/or enhancing the fixation of the prosthesis.

Figure 11:
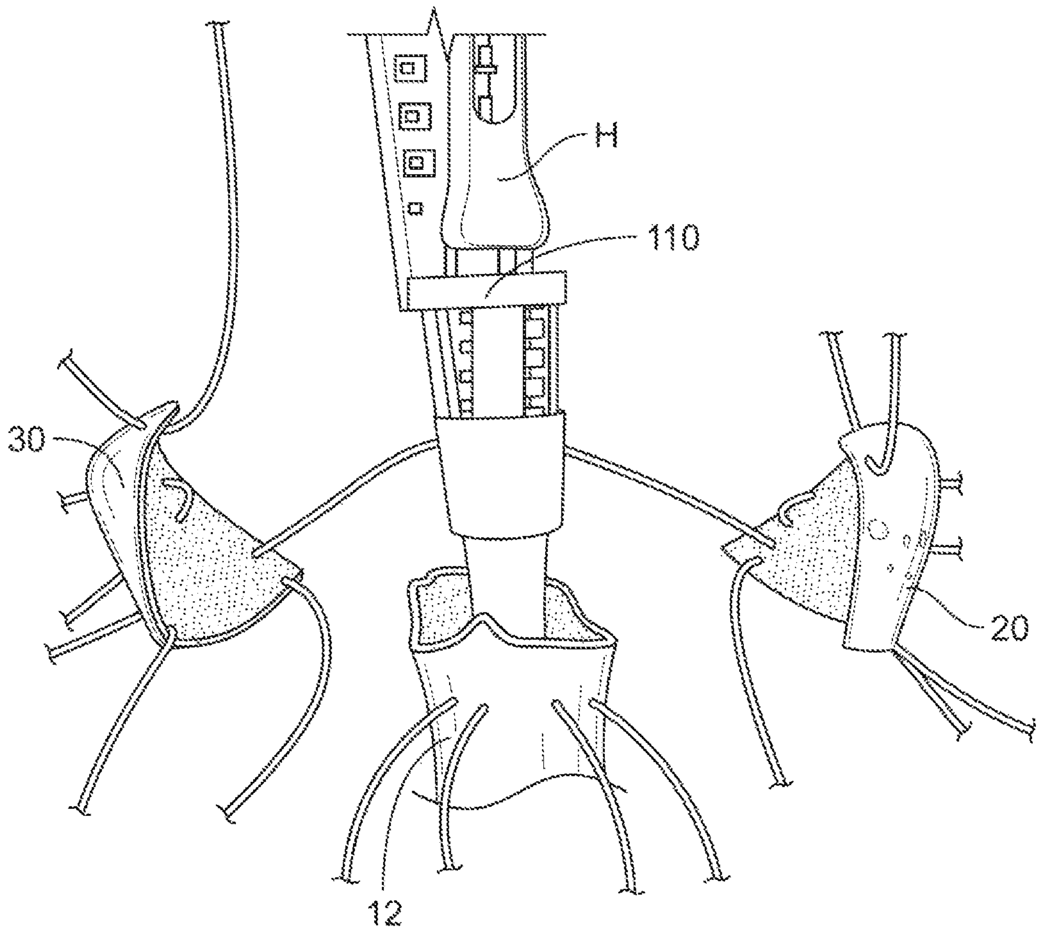

Referring now to FIG. 11, an example is shown of various suture wires passing through fragments 20, 30 and through the proximal portion 110 of prosthetic humeral stem 100, which is illustrated in the figure as being coupled to a handle H. With the suture wires threaded through the suture apertures in fragments 20, 30 (and optionally proximal humerus 12) and through the desired suture apertures in the proximal portion 110 of prosthetic humeral stem 100, the suture wires may be pulled while (or after) the prosthetic humeral stem 100 is implanted into the proximal humerus 12 to draw the fragments 20, 30 into place against each other and/or the proximal portion 110 of the prosthetic humeral stem 100. The sutures may then be tied, as described above, to help hold the fragments 20, 30 in place against the prosthetic humeral stem 100. Although not illustrated, a prosthetic humeral head (or a prosthetic humeral cup in the case of a reverse shoulder arthroplasty) may be coupled to the prosthetic humeral stem 100, for example via implant recess 114 shown in FIGS. 2B-C.

Referring again to FIGS. 9-10, although not illustrated, the proximal portions of fragments 20, 30 and distal portion 14 of proximal humerus 12 may be machined to have interlocking mating features to interlock with one another. Still further, although not shown, the distal portion 14 of proximal humerus 12 may be machined to have a surface that corresponds to the exterior surface of the prosthetic humeral stem 100 where the prosthetic humeral stem 100 will contact the distal portion 14 after implantation. Examples of such machining are described in greater detail below.

Figure 12:
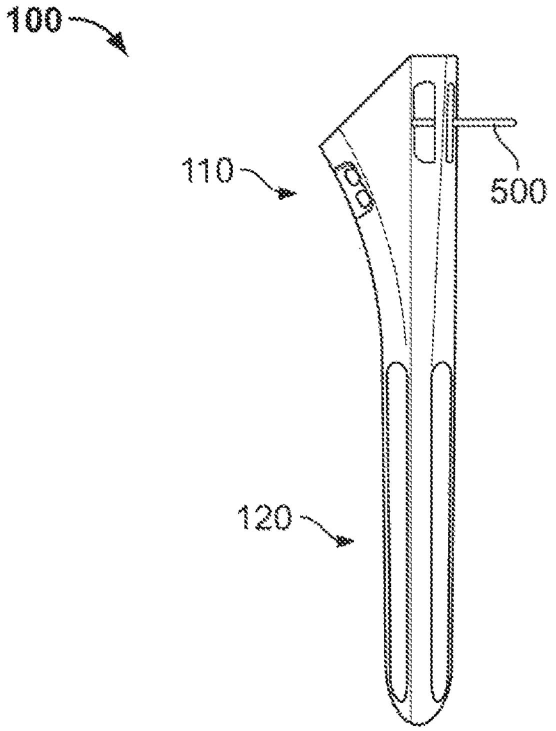
FIG. 12 is a perspective view of a suture needle being passed through a portion of the stem implant of FIG. 2A.
Figure 13:
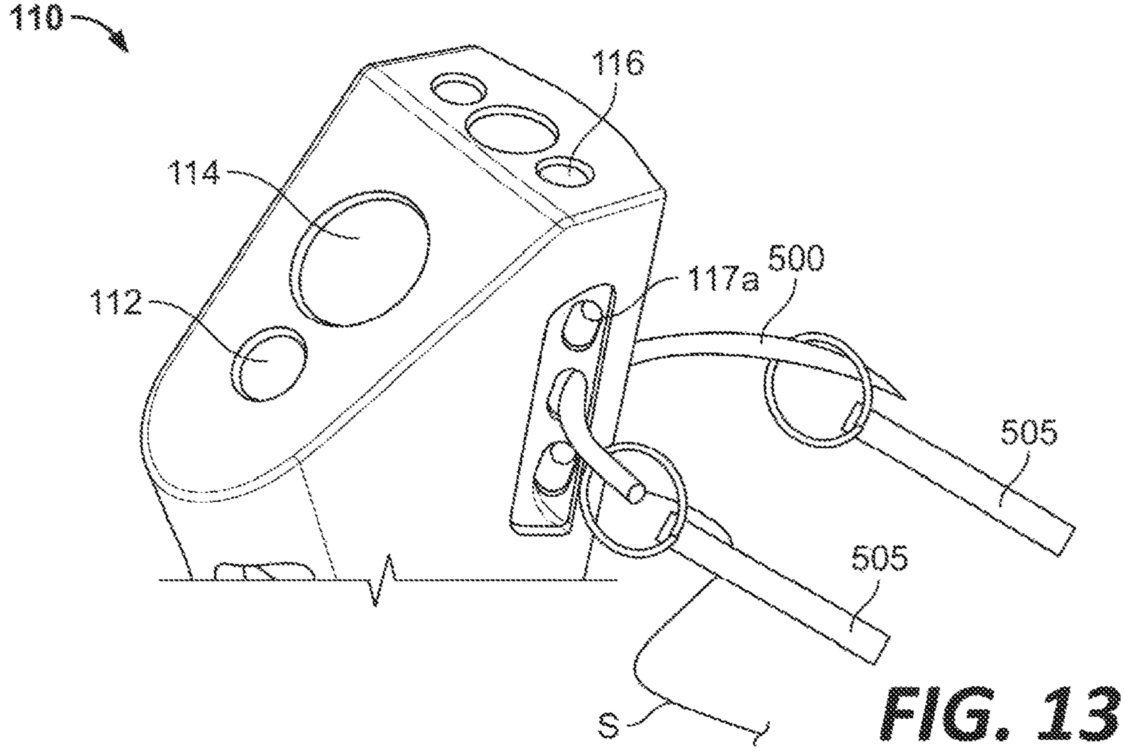
FIG. 13 is an enlarged view of a portion of the stem implant of FIG. 12.

As noted above, suture wires may be used to help hold together fragments 20, 30 of the proximal humerus, and if stem implant 100 is utilized, suture wires may help hold the fragments 20, 30 to the implant 100. As also noted above, while such suture wires may be placed manually, in other embodiments the suture wires may be placed with the assistance of CAS system 311. FIG. 12 illustrates a leading end of a suture needle 500 passing through one of the suture holes 117*a* in proximal portion 110 of the prosthetic stem implant 100. As shown in the enlarged illustration in FIG. 13, the suture needle 500 may be curved, with a sharp leading end and a suture S coupled to the trailing end of the suture needle 500. Because the dimensions of the prosthetic stem implant 100 are known (e.g. via prior scanning or uploading of the information, or via probing of the stem implant 100), and because the precise positions, orientations and dimensions all of the suture apertures machined into the various fragments 20, 30 are known via CAS system 311, the CAS system 311 may be utilized to precisely thread one or more sutures S through the fragments 20, 30 and/or the prosthetic stem implant 100. The position and orientation of the prosthetic stem implant 100 at the time of suturing may be determined by tracking the prosthetic stem implant 100 via a tracker, and/or by determining the position of the prosthetic stem implant via probing two or more surfaces of the prosthetic stem implant 100 to allow the CAS system 311 to understand the position and orientation of the prosthetic stem implant 100. As shown in FIG. 12, one or more manipulators or arms 505 may be operatively coupled to the CAS system 311, for example as the surgical instrument 352. The dimensions of the arms 505 may be known by the CAS system 311 so that the CAS system 311 understands the position of the arms 505 relative to the prosthetic stem implant 100 and the proximal humerus 12 (including any fragments 20, 30). The dimensions of the suture needle 500, which may be gripped and moved by and between arms 505, may also be known and tracked by the CAS system 311, so that the CAS system 311 understands where the tip of the suture needle 500 is at all times. With all of this information, the CAS system 311 may manipulate the arms 505 to move the suture needle 500 through the desired suture apertures in the proximal humerus 12, the fragments 20, 30, and/or any of the suture holes (such as suture holes 117*a*) in the proximal portion 110 of the prosthetic stem implant 100 in order to position all of the sutures S autonomously (or semi-autonomously). For example, a first arm 505 may primarily function to pass the suture needle 500 through a desired suture hole, with a second arm 505 primarily functioning to pull the suture needle 500 through the hole after it begins to pass through the hole. Although suture arms 505 are shown as straight elements with hoops at terminal ends, other structures may be suitable, such as grips, clamps, forceps, etc. Such automated suturing my significantly reduce the time necessary for positioning all of the sutures S in the desired positions and through the desired components compared to manual suturing. It should be understood that this autonomous (or semi-autonomous) suturing method may be used for any embodiment herein that calls of securing bone or bone fragments with sutures.

Referring again to FIG. 8, the machining of the fragments 20, 30 and/or the proximal humerus 12 is not shown in great detail. It should be understood that the machining may be similar to that shown and described in connection with FIG. 3, or may take other forms. FIGS. 14-23 show various other types of machining that may be suitable, and it should be understood that any of the machining patterns described herein may be used for embodiments that include or exclude the use of a prosthetic implant such as prosthetic stem implant 100.

Figure 14:
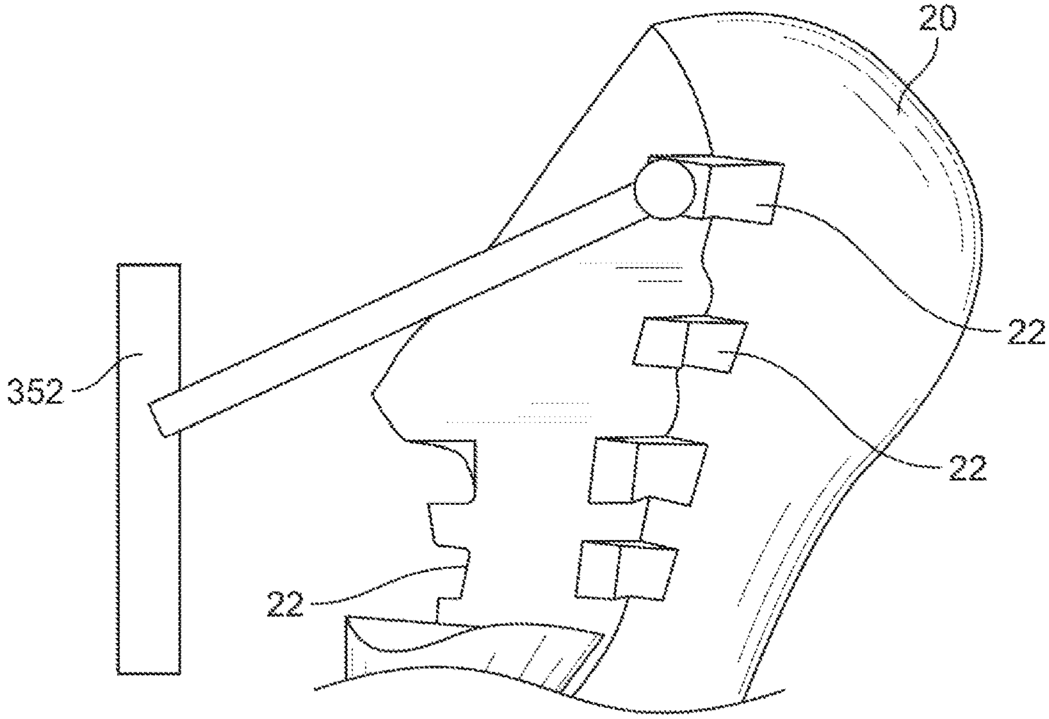
FIGS. 14-15 are schematic views of grooves and ridges being machined into bone fragments.
Figure 15:
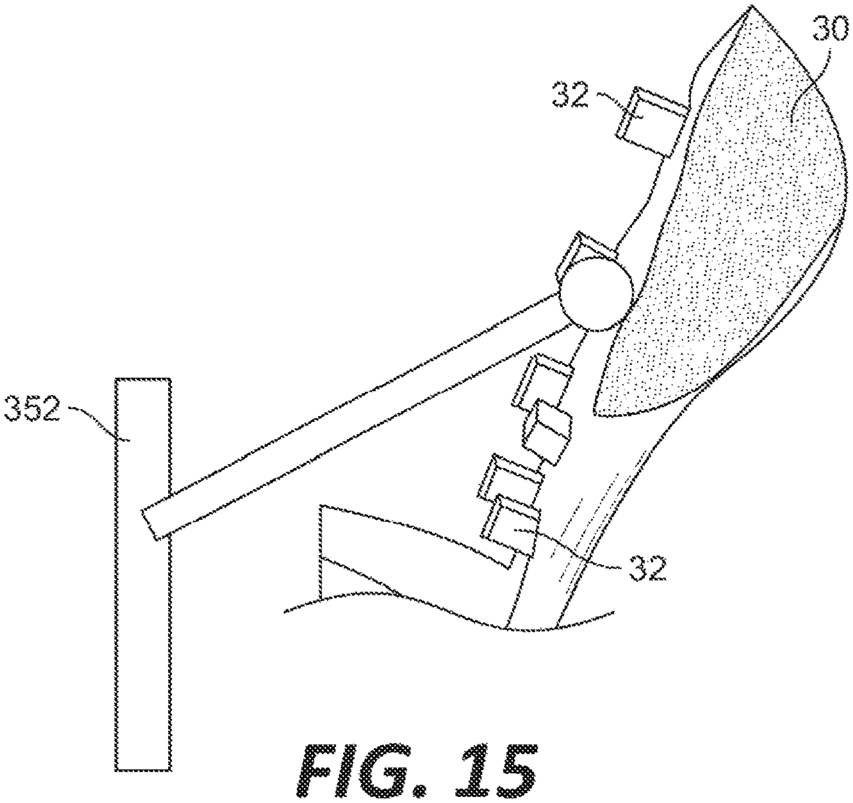

FIGS. 14-15 illustrate grooves and ridges machined into fragments 20, 30. For example, FIG. 14 illustrates a tool such as surgical tool 352 of CAS system 311 machining a plurality of notches, pockets, recesses, or grooves 22 into bone fragment 20. In the illustrated embodiment, a first plurality of grooves 22 are created vertically (e.g. along the superior-inferior direction) at a corner or edge of the fragment 20, for example where the native-shaped fragment 20 transitions into the broken interior surface of the fragment 20 that would not be visible but for the fracture. In the illustrated embodiment, this first plurality of grooves 22 includes four grooves spaced apart from one another, each groove 22 having a substantially rectangular profile. The illustrated embodiment also includes a second plurality of grooves created vertically at another corner or edge of the fragment opposite the first corner or edge. As illustrated, the second plurality of grooves includes two grooves 22 and similarly include a rectangular profile. FIG. 15 illustrates a tool such as surgical tool 352 of CAS system 311 machining a plurality of protrusions, projections, bulges, or ridges 32 that have a shapes and positions complementary to the shapes and positions of the grooves 22. In other words, in the illustrated embodiment, the ridges 32 are substantially rectangular shaped projections aligned in a first vertical group (e.g. a total of four) at an edge of fragment 30 and a second vertical group (e.g. a total of two) at an opposite edge of fragment 30.

Figure 16:
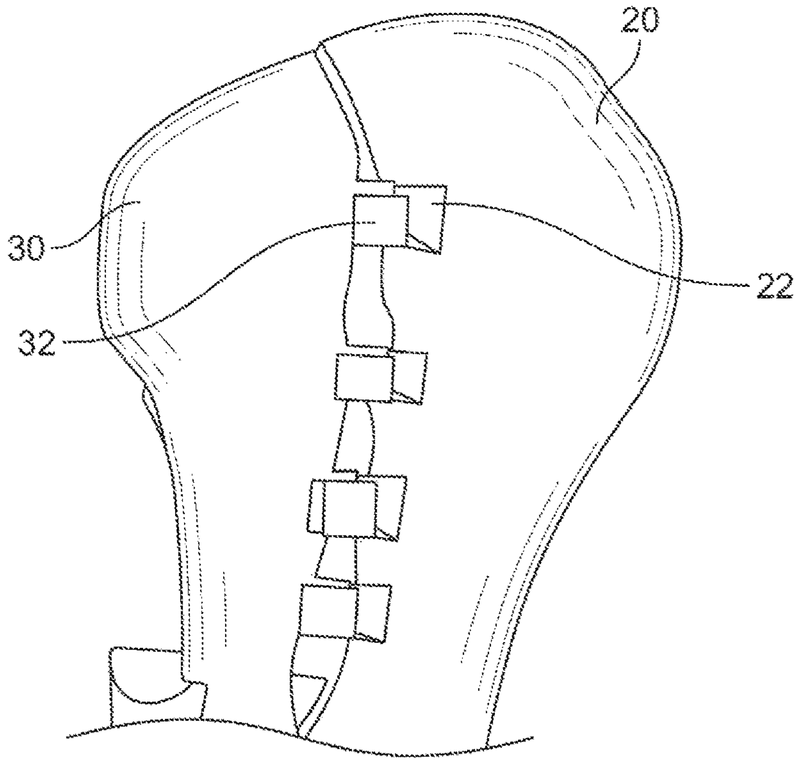
FIGS. 16-17 are perspective views of the bone fragments of FIGS. 14-15 being coupled to each other and to the prosthetic stem implant of FIG. 2A.
Figure 17:
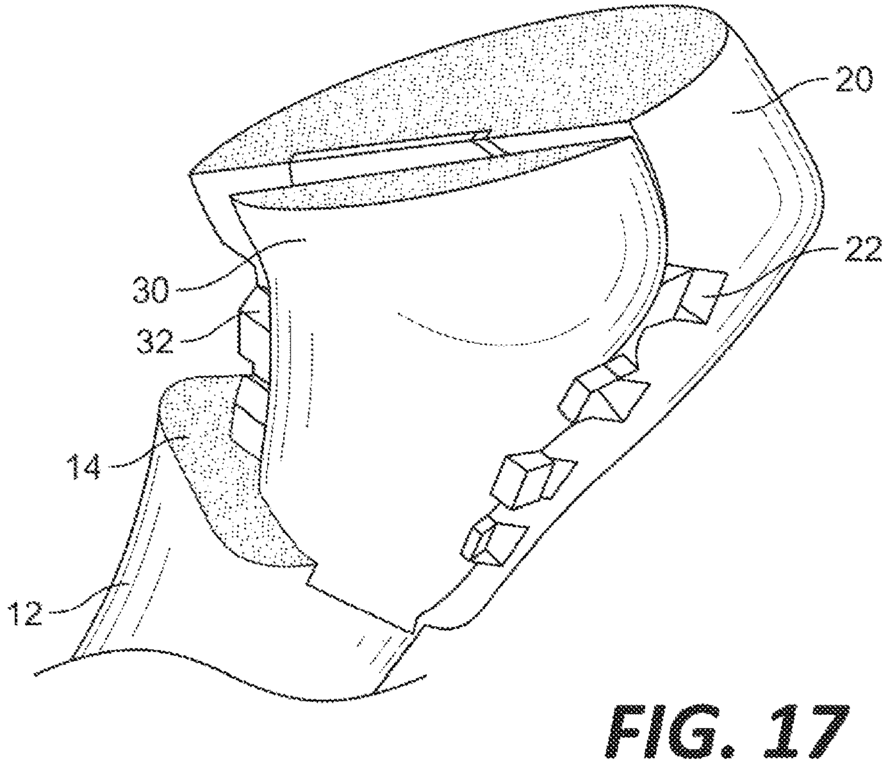

Referring to FIG. 16, when fragment 20 is engaged with fragment 30, each ridge 32 fits within a corresponding groove 22 to interlock the fragments 20, 30 together. In this illustrated example, the interlocking configuration will restrict motion of the fragment 20 relative to fragment 30 along the humeral axis (e.g. in a superior-to-inferior direction). Depending upon the positioning of the ridges 32, the interlocking configuration may also restrict motion of the fragment 20 relative to fragment 30 in the medial-lateral direction. It should be understood that the grooves 22 and ridges 32 may be used alone (with or without additional suture holes similar to those described above) if the bone fragments 20, 30 are to be coupled each other without an intervening prosthesis such as prosthetic humeral stem 100. However, in some embodiments, as shown in FIG. 17, the fragments 20, 30 may be machined to include additional surfaces that have contours that complement the exterior contours of an implant, such as prosthetic humeral stem 100, so that the fragments 20, 30 closely fit over the prosthetic humeral stem 100 and also interlock with each other, for example via the mating between the grooves 22 and ridges 32.

Figure 18:
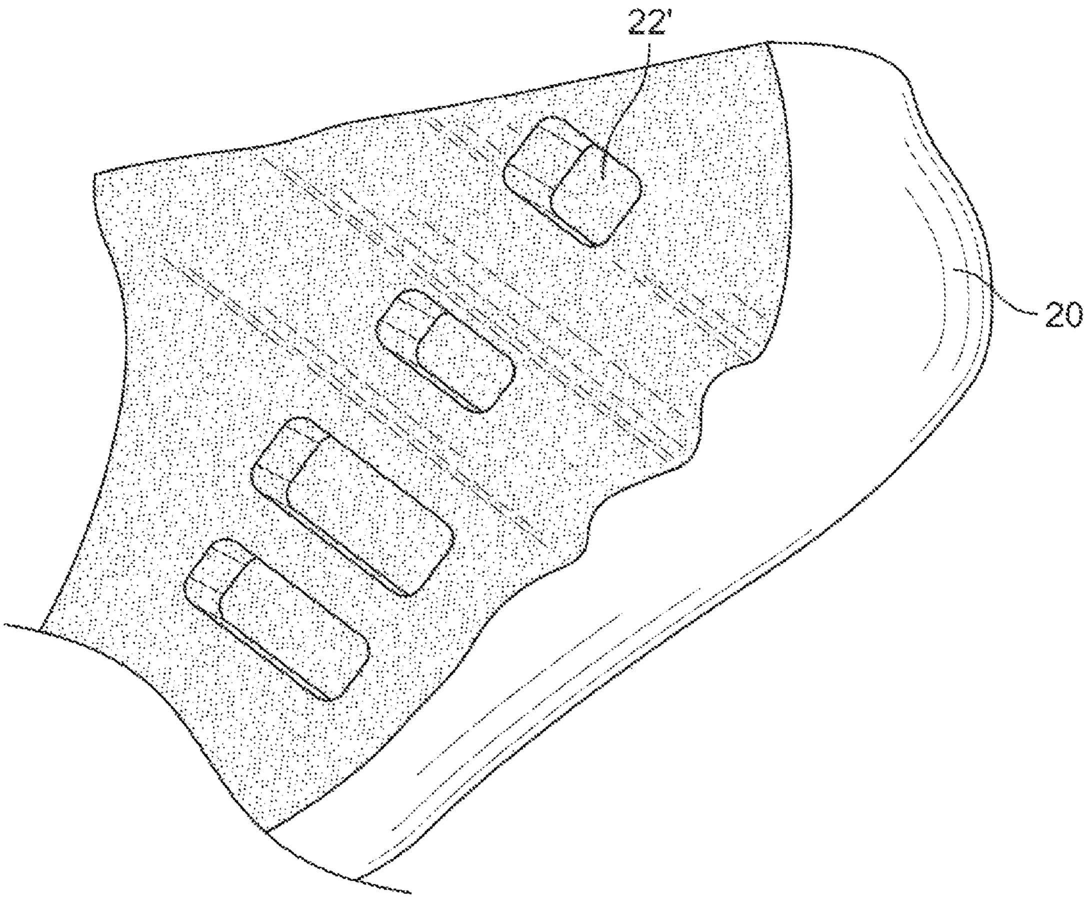
FIG. 18 is a perspective view of an alternate type of groove machined into a bone fragment.

Referring now to FIG. 18, fragment 20 is illustrated with a plurality of grooves 22' that are substantially similar in shape to grooves 22, but are instead positioned fully within the interior face of the fragment 20. In other words, grooves 22' have a rectangular profile and extend a depth into the fragment 20, with the grooves 22' being bounded on all sides by fragment 20. With this configuration, fragment 30 may be machined with complementary protrusions and, when fragments 20, 30 engage each other and the protrusions of fragment 30 insert into the grooves 22' of fragment 20, relative movement between the fragments will be restricted both along the humeral axis (e.g. superior-to-inferior) as well as along an axis transverse the humeral axis (e.g. medial-to-lateral). In other words, because the grooves 22' of fragment 20 are bounded on all sides by bone of fragment 20, protrusions received within the grooves 22' will not be able to move in any direction other than along the axis of the protrusion, which may be restricted via adhesives and/or suture wires that hold fragments 20, 30 together during healing. Although not shown in FIGS. 14-18, additional protrusions may be machined into fragments 20, 30 in order to be partially or fully received within any of the suture pockets in prosthetic humeral stem 100, such as suture pockets 119*a*. In other words, the suture pockets (e.g. suture pockets 119*a*) may have a recessed shape, and protrusions having a shape complementary to the suture pockets may be created in the fragments 20, 30 so that those protrusions fit within and/or engage the suture pockets. Still further, although not shown in FIGS. 14-18, mating features similar to any of those described above (or below) may be machined into the humeral bearing surface 14 at the proximal end of the proximal humerus 12 where the fracture occurred, with complementary mating features machined into the distal portions of fragments 20, 30 that will contact the humeral bearing surface 14. As noted above, for any of the machining on fragments 20, 30, the fragments 20, 30 may be held in a fixture, such as fixture 400, with CAS system 311 autonomously or semi-autonomously machining the mating features into the fragments 20, 30.

Figure 19:
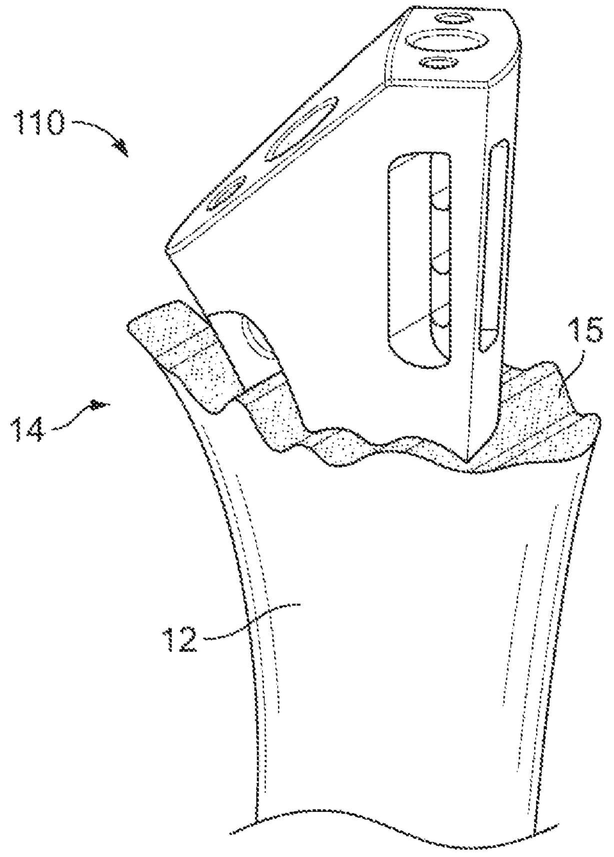
FIG. 19 is a perspective view of the prosthetic stem implant of FIG. 2A implanted into a proximal humerus

FIG. 19 illustrates a fractured proximal humerus 12 in which prosthetic stem implant 100 has been implanted. Various fragment of the proximal humerus 12 are not illustrated in FIG. 19. The bearing surface 14 of proximal humerus 12, which in FIG. 19 is the proximal end of the proximal humerus 12 where the fractured occurred, is illustrated with mating features 15 having been machined therein. In the illustrated embodiment, the mating features 15 are alternating peaks and troughs or grooves and notches. As with other mating features in the bone described herein, the mating features 15 illustrated in FIG. 19 may be machined into the proximal end of the proximal humerus 12 using a system similar to CAS system 311, for example while the patient's arm is held stationary. As should be understood, the shape, position, and orientation of the mating features 15 may be pre-operatively or intra-operatively planned, with corresponding and/or complementary mating features planned to be machined into the distal end of any fragments that will contact the mating features 15 of proximal humerus 12.

Figure 20:
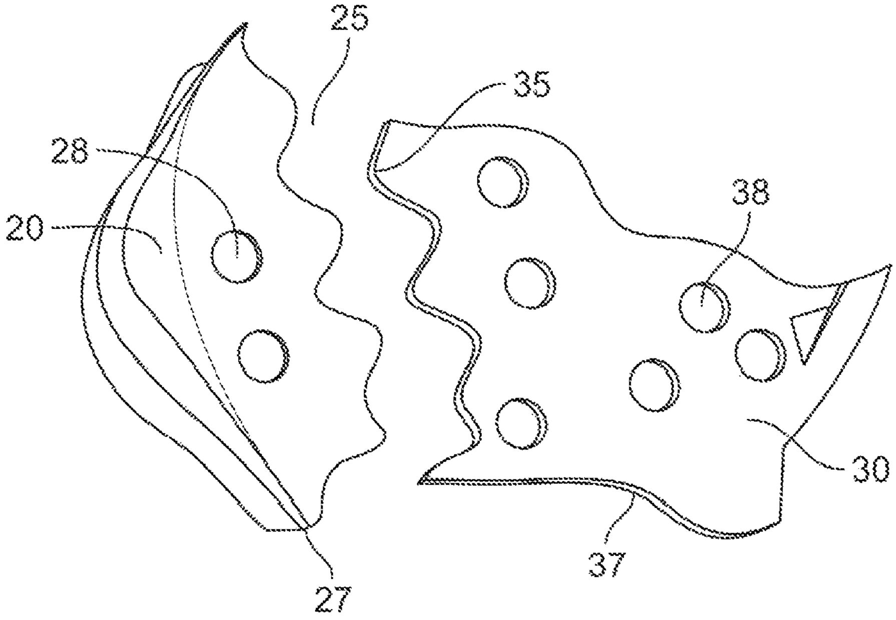
FIGS. 20-21 are views of fragments of a proximal humerus.
Figure 21:
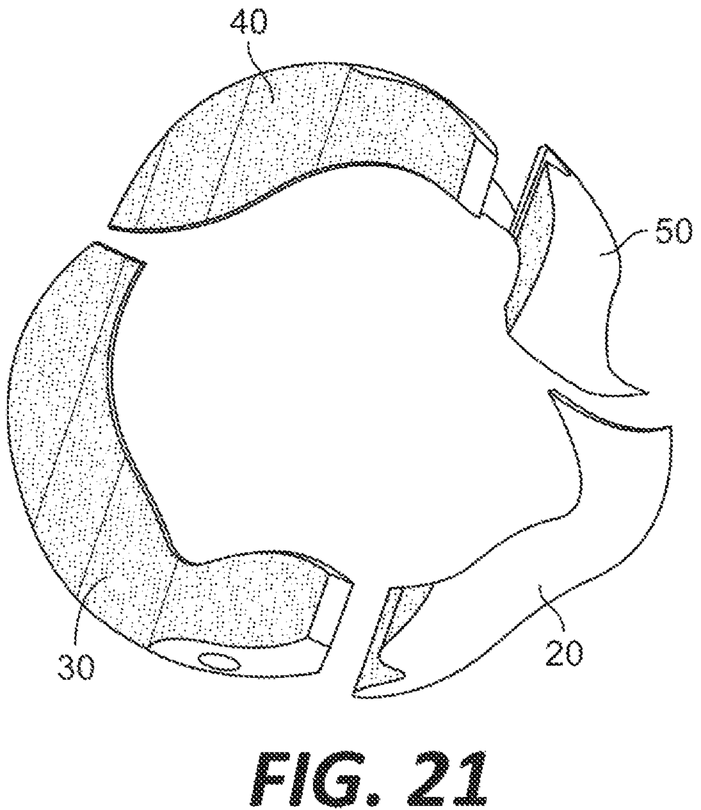

FIGS. 20-21 are side and top views, respectively, of fragments 20, 30, 40, 50 of the humeral head that have fractured away from the proximal humerus 14 of FIG. 19. Any of the above-described mating features may be formed into fragments 20, 30, 40, 50. For example, FIG. 20 shows the interior surface of two fragments 20, 30 after various features have been machined therein. Any number of sutures holes 28, 38 may be machined into fragments 20, 30, in any desired positions, and the suture holes 28, 38 may be similar or identical to suture holes 280, 380. For example, although suture holes 28, 38 may be formed manually, the number and position of suture holes may be pre-operatively or intra-operatively planned, and may be formed according to that plan using a system similar to CAS system 311. The fragments 20, 30 may he held in a fixture similar to fixture 400 during the machining, and the process may be similar to that described above for other embodiments. The suture holes 28, 38 may be optimally positioned to allow one or more sutures to pass through the suture holes 28, 30 and/or through corresponding suture holes in the proximal portion 110 prosthetic stem implant 100 to allow for the fragments 20, 30 to be secured to one another and to the prosthetic stem implant 100. It should be understood that any features described in connection with fragments 20, 30 above or below may be similarly included in fragments 40, 50.

Still referring to FIG. 20, mating features 25, 35 may be machined into fragments 20, 30 respectively. In the illustrated embodiment, mating features 25, 35 take the form of complementary peaks and troughs, although any other complementary mating features may be suitable, such as the ribs and grooves described above, or any other suitable feature, including dovetail connections, etc. Mating features 25, 35 may help to secure fragment 20 with respect to fragment 30 in an interlocking fashion. Additional mating features 27, 37 may be machined into the distal end of fragments 20, 30 that will engage the mating features 15 in the proximal end of the bearing surface 14 of proximal humerus 12. In the illustrated example, the mating features 27, 37 include peaks and troughs complementary to the peaks and troughs of mating features 15, but it should be understood that other shaped mating features such as those described above may be suitable alternatives. Further, although not illustrated in FIG. 20, the interior surfaces of fragments 20, 30 may be machined to have an interior surface shape that is complementary to the exterior shape of the proximal portion 110 of the prosthetic stem implant 100 so that the fragments 20, 30 will closely conform to the prosthetic stem implant 100.

Figure 22:
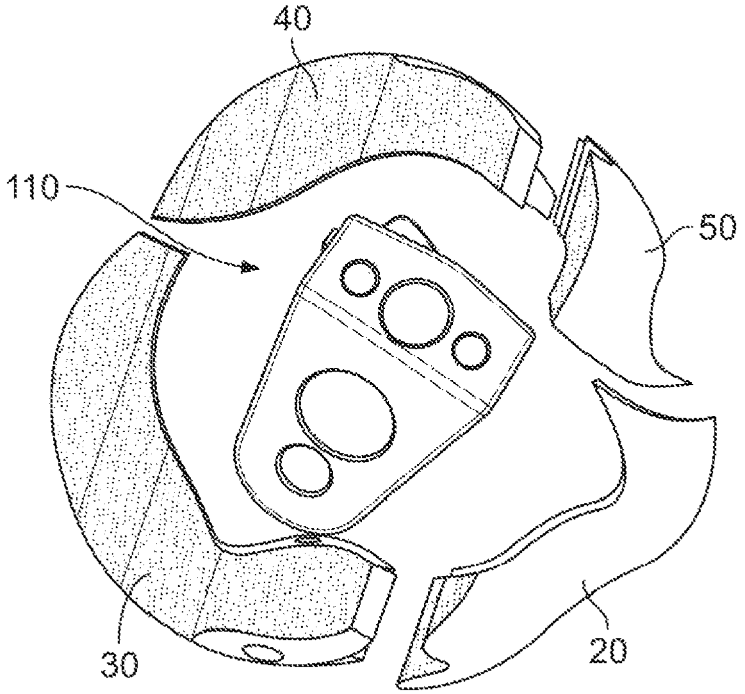
FIGS. 22-23 are views of fragments of the proximal humerus adjacent the prosthetic stem implant of FIG. 2A.
Figure 23:
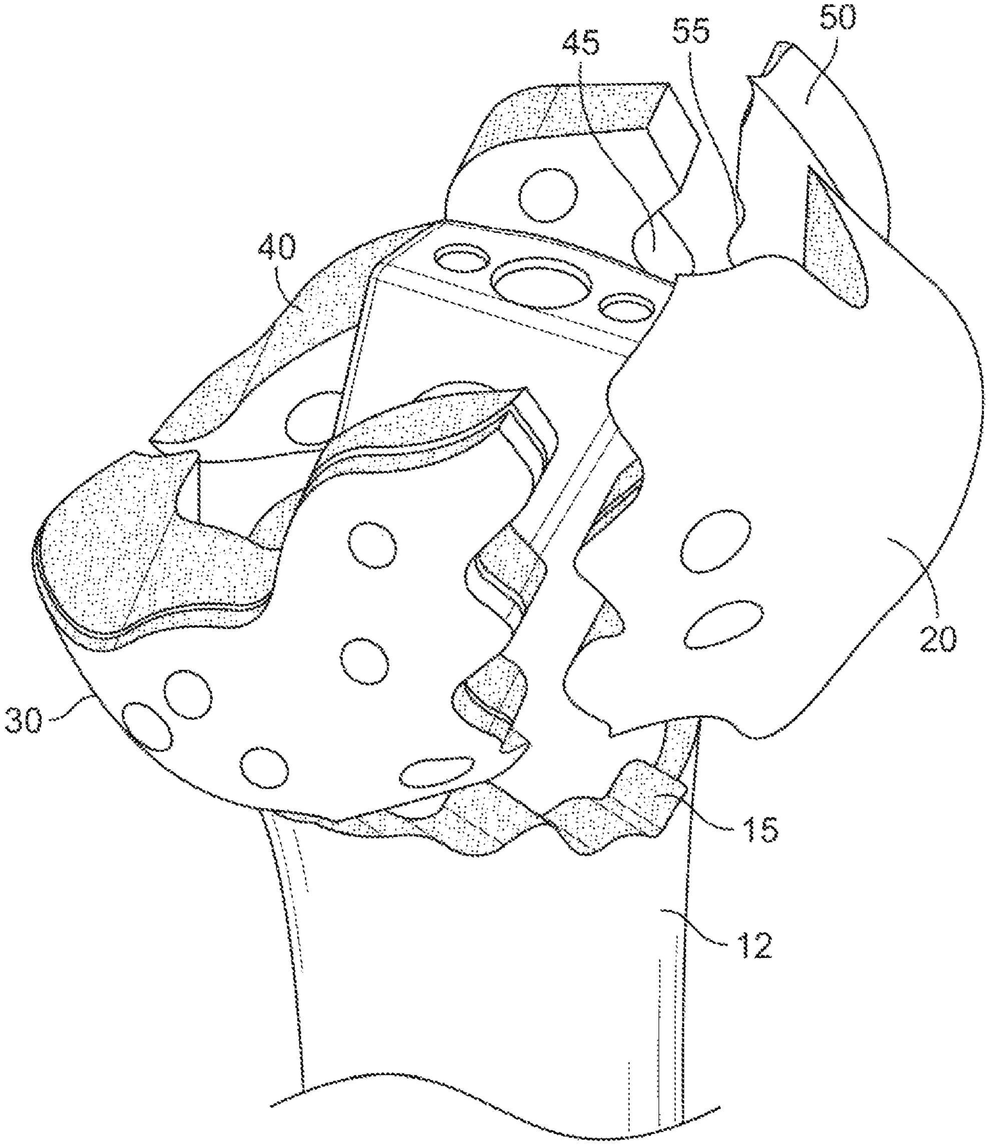

FIGS. 21-22 illustrate top views of fragments 20, 30, 40, 50 positioned adjacent onc another in near-engagement, with and without the prosthetic stem implant 100 illustrated, respectively. FIG. 23 illustrates a perspective view of the fragments 20, 30, 40, 50 positioned adjacent one another and the prosthetic stem implant 100 in near-engagement. As can be seen in FIGS. 21-23, the various mating features 25, 35, 45, 55 are complementary and will interlock with one another when the fragments 20, 30, 40, 50 are engaged with each other, the proximal humerus 12, and the prosthetic stem implant 100. Similarly, the distal ends of the fragments 20, 30, 40, 50 will all interlock with the mating features 15 in the exposed proximal end surface of the proximal humerus 12 for additional interlocking engagement. Finally, one or more of the fragments 20, 30, 40, 50 may have interior shapes that are machined to be complementary with the surfaces of the proximal portion 110 of the prosthetic humeral stem 100 which the fragments will contact. As with embodiments described above, one or more suture wires may be manually or automatically threaded through the suture holes in the fragments 20, 30, 40, 50 and/or the proximal portion 110 of the prosthetic stem implant 100. As the sutures are tightened, the fragments 20, 30, 40, 50 may be drawn together toward one another and toward the proximal portion 110 of the prosthetic humeral stem 100 into close engagement. This close engagement may reduce micro-motion, enhance bone ingrowth, and provide for better overall fixation of the fracture and/or shorter healing and/or recovery time. As with embodiments described above, adhesives such as bone cement may be used between any of the fragments 20, 30, 40, 50, the proximal surface of the proximal humerus 12, and/or the proximal portion 110 of the prosthetic humeral stem 100 to provide for additional fixation. Following fixation of the fragments 20, 30, 40, 50 to each other, to the proximal humerus 12, and to the prosthetic humeral stem 100, a prosthetic humeral head may be coupled to the prosthetic humeral stem 100. However, it should be understood that the concepts described above in connection with FIGS. 19-23 may be similarly provided in a fracture repair that does not include a prosthetic humeral component, with certain modifications as would be understood by a person skilled in the art.

Figure 24:
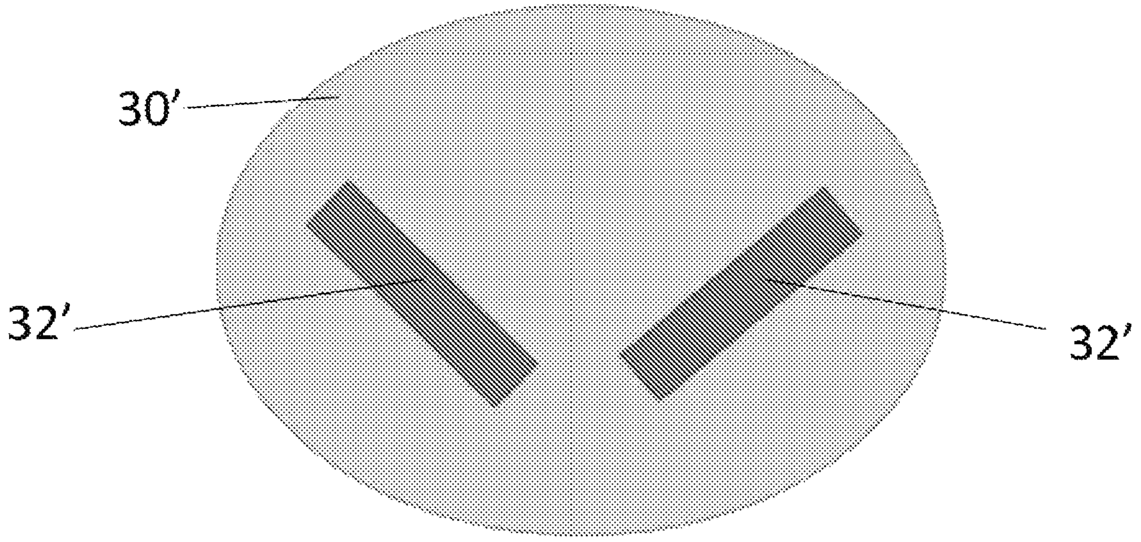
FIG. 24 is a rear view of a bone fragment having "V"-shaped interlocking features formed therein.

FIG. 24 illustrates an alternate version of an interlocking features, similar to ridges 32 and grooves 22 of FIG. 16, but with different orientations. For example, FIG. 24 illustrates a side view of an interior surface of a fragment 30' that includes outwardly extending ridges 32' that have been robotically machined into the fragment 30'. Although not illustrated, complementary grooves could be robotically machined into a corresponding fragment, with those complementary grooves adapted to receive the ridges 32' therein. While the ridges 32 and grooves 22 of FIG. 16 extend substantially horizontal relative to the humeral axis, ridges 32' of FIG. 24 together form a general “V”-shape, where each ridge 32' extends at about an equal but opposite oblique angle relative to the humeral axis (which is from top to bottom in the view of FIG. 24). This general “V”-shape may help restrict both axial and lateral movement of fragment 30' when the ridges 32' thereof are interlocked with complementary grooves of another humeral fragment.

Figure 25:
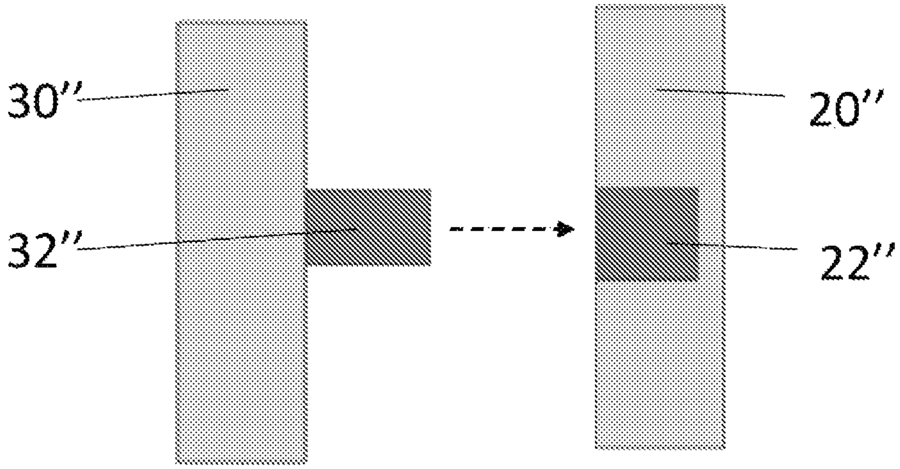
FIG. 25 is a side view of two bone fragments having cylindrical interlocking features formed therein.

Still other interlocking features may be desirable in some embodiments. For example, in some scenarios, it may be preferable to allow for an amount of rotational motion between two fragments as they interlock and as they are drawn together to be secured to each other (and/or to an intermediary prosthetic humeral stem). For example, FIG. 25 illustrates two fragments 20" and 30" that include a protrusion 32" and slot 22" to receive the protrusion 32" therein. In the side view of FIG. 25, protrusion 32" is a substantially cylindrical protrusion 32" that has been robotically machined into fragment 30", while slot 22' is a complementary and substantially cylindrical slot configured to receive the protrusion 32". While the protrusion 32" is received within slot 22", fragment 30" may be capable of rotating about an axis defined by the protrusion 32" relative to fragment 20". This rotation may allow for additional flexibility for positioning the fragment 20" relative to the other fragment 30", with adhesives and/or suture wires being used to help maintain the desired relative position between the fragments 20" and 30". It should be understood that further types of interlocking features of different numbers, shapes, and positions may also be suitable.

Although the disclosure above is described in the context of repairing a fracture of a humeral head, with or without a corresponding humeral prosthesis implant, it should be understood that the invention is not so limited. For example, the disclosure may be applied to the repair of fractures of other bones, with or without a corresponding prosthesis being implanted. For example, the disclosure may be used in connection with the repair of a femoral head fracture, with or without a corresponding implantation of a prosthetic femoral stem. Nor are the concepts limited to fractures of the humerus and femur, or to fracture repairs in connection with prosthetic stem implants. For example, the concepts may be applied to fractures that are being repaired with bone plates or nails, as well as other joint repairs that utilized implants other than stem-style implants.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of repairing a fractured bone having at least a first bone segment and a second bone segment, the method comprising:

positioning an implant in the fractured bone, the implant having a first end with a first surface portion and a second surface portion;

robotically machining the first bone segment of the fractured bone to include a first implant-facing surface that is substantially a negative of the first surface portion of the first end of the implant;

robotically machining the second bone segment of the fractured bone to include a second implant-facing surface that is substantially a negative of the second surface portion of the first end of the implant;

robotically machining the first bone segment and the second bone segment so that the first bone segment has a first interlocking surface and the second bone segment has a second interlocking surface shaped to interlock with the first interlocking surface; and positioning the first bone segment and the second bone segment with respect to the first end of the implant so that (i) the first implant-facing surface is in contact with the first surface portion of the first end of the implant, (ii) the second implant-facing surface is in contact with the second surface portion of the first end of the implant, and (iii) the first interlocking surface interlocks with the second interlocking surface.

2. The method of claim 1, wherein the first implant is any of a bone plate, a nail and a prosthetic stem.

3. The method of claim 1, wherein the first bone segment is held within a fixture while the first bone segment is robotically machined to include the first implant-facing surface and the first interlocking surface.

4. The method of claim 3, wherein at least one tracking device is coupled to the fixture while the first bone segment is held within the fixture.

5. The method of claim 4, further comprising registering a position of the first bone segment while it is held within the fixture and prior to robotically machining the first bone segment.

6. The method of claim 1, wherein the first implant is configured to connect to a joint prosthesis.

7. The method of claim 1, wherein when the first interlocking surface interlocks with the second interlocking surface, the first and second interlocking surfaces restrict the first bone segment from moving in medial and lateral directions relative to the second bone segment.

8. The method of claim 1, further comprising machining the first bone segment to have a first hole and machining the second bone segment to have a second hole.

9. The method of claim 8, further comprising passing at least one suture wire through the first hole, through the second hole, and through an implant hole positioned within the first end of the implant.

10. The method of claim 9, further comprising:

after the at least one suture wire is passed through the first hole, through the second hole, and through the implant hole, manipulating the at least one suture wire to draw the first bone segment and the second bone segment into contact with the first end of the implant.

* * * * *